United States Patent
Finch et al.

(10) Patent No.: US 8,557,797 B2
(45) Date of Patent: Oct. 15, 2013

(54) TRIAZOLOPYRIDINE DERIVATIVES AND THEIR THERAPEUTIC USE

(75) Inventors: Harry Finch, Slough (GB); John Montana, Slough (GB); Monique Bodil Van Niel, Slough (GB); Chi-Kit Woo, Slough (GB); Jamie Knight, Slough (GB); Bohdan Waszkowycz, Slough (GB)

(73) Assignee: Chiesi Farmaceutici S.p.A., Parma (IT)

( * ) Notice: Subject to any disclaimer, the term of this patent is extended or adjusted under 35 U.S.C. 154(b) by 36 days.

(21) Appl. No.: 13/201,716

(22) PCT Filed: Feb. 16, 2010

(86) PCT No.: PCT/GB2010/050257
§ 371 (c)(1),
(2), (4) Date: Dec. 19, 2011

(87) PCT Pub. No.: WO2010/094956
PCT Pub. Date: Aug. 26, 2010

(65) Prior Publication Data
US 2012/0088763 A1    Apr. 12, 2012

(30) Foreign Application Priority Data

Feb. 17, 2009 (GB) .................................. 0902651.9
May 11, 2009 (GB) .................................. 0908069.8

(51) Int. Cl.
*A61K 31/535* (2006.01)
*A01N 43/54* (2006.01)
*C07D 413/04* (2006.01)
*C07D 239/02* (2006.01)

(52) U.S. Cl.
USPC ........ 514/122; 514/234.5; 544/319; 544/122; 544/123

(58) Field of Classification Search
USPC ................ 544/122, 123, 319; 514/234.5, 259
See application file for complete search history.

(56) References Cited

U.S. PATENT DOCUMENTS

| | | |
|---|---|---|
| 8,450,314 B2 | 5/2013 | Beswick et al. |
| 2005/0075365 A1 | 4/2005 | Braganza et al. |
| 2006/0035922 A1 | 2/2006 | Mathias et al. |
| 2009/0012079 A1 | 1/2009 | Lewthwaite et al. |
| 2009/0215817 A1 | 8/2009 | Rucker et al. |
| 2009/0239899 A1 | 9/2009 | Mathias et al. |

FOREIGN PATENT DOCUMENTS

| | | |
|---|---|---|
| WO | 2004 072072 | 8/2004 |
| WO | 2006 018718 | 2/2006 |
| WO | 2006 018727 | 2/2006 |
| WO | 2007 091152 | 8/2007 |

OTHER PUBLICATIONS

Dumas, J. et al., "Recent Developments in the Discovery of Protein Kinase Inhibitors From the Urea Class", Current Opinion in Drug Discovery and Development, vol. 7, No. 5, pp. 600-616, XP-009063727, (Sep. 1, 2004).
Jerome, K. D. et al., "Continued Exploration of the Triazolopyridine Scaffold as a Platform for P38 MAP Kinase Inhibition", Bioorganic & Medicinal Chemistry Letters, vol. 20, No. 2, pp. 469-473, XP-026812512, (Jan. 15, 2010).
International Search Report Issued Jun. 22, 2010 in PCT/GB10/050257 filed Feb. 16, 2010.
U.S. Appl. No. 13/701,989, filed Dec. 4, 2012, Woo, et al.
U.S. Appl. No. 13/708,324, filed Dec. 7, 2012, Van Niel, et al.
U.S. Appl. No. 13/708,191, filed Dec. 7, 2012, Van Niel, et al.
U.S. Appl. No. 13/201,716, filed Dec. 19, 2011, Finch, et al.

*Primary Examiner* — Rebecca Anderson
(74) *Attorney, Agent, or Firm* — Oblon, Spivak, McClelland, Maier & Neustadt, L.L.P.

(57) ABSTRACT

Compounds of formula (I) are inhibitors of p38 MAP kinase, useful as anti-inflammatory agents in the treatment of inter alia, diseases of the respiratory tract wherein; $R^1$ is $C_1$-$C_6$ alkyl, $C_3$-$C_6$ cycloalkyl, phenyl which is optionally substituted, 5- or 6 membered monocyclic heteroaryl which is optionally substituted, or a radical of formula (II) wherein n is 1 or 2, and $R^3$ and $R^4$ are independently H or $C_1$-$C_6$ alkyl, or $R^3$ and $R^4$ taken together with the nitrogen to which they are attached form a 6-membered heterocyclic ring optionally containing a further heteroatom selected from N and O; Y is —O— or —S(O)$_p$— wherein p is 0, 1 or 2; A is an optionally substituted divalent arylene radical, or a mono- or bicyclic heteroarylene radical, or a $C_3$-$C_6$ divalent cycloalkylene radical having 5 or 6 ring atoms, or a piperidinylene radical wherein the ring nitrogen is linked to $R^2$NHC(═O)W—; W is a bond, —NH— or —C($R^A$)($R^B$), wherein $R^A$ and $R^B$ are independently H, methyl, ethyl, amino, hydroxyl or halo; and $R^2$ is a radical as defined in the claims.

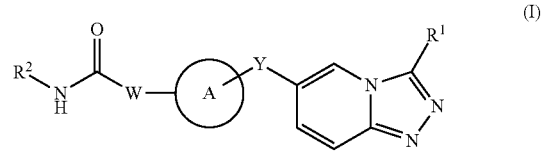

(I)

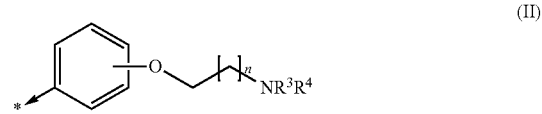

(II)

20 Claims, 1 Drawing Sheet

TRIAZOLOPYRIDINE DERIVATIVES AND THEIR THERAPEUTIC USE

This invention relates to compounds and compositions that are p38 MAPK inhibitors, useful as anti-inflammatory agents in the treatment of, inter alia, diseases of the respiratory tract.

BACKGROUND TO THE INVENTION

Mitogen activated protein kinases (MAPK) constitute a family of proline-directed serine/threonine kinases that activate their substrates by dual phosphorylation. There are four known human isoforms of p38 MAP kinase, p38α, p38β, p38γ and p38δ. The p38 kinases, which are also known as cytokine suppressive anti-inflammatory drug binding proteins (CSBP), stress activated protein kinases (SAPK) and RK, are responsible for phosphorylating (Stein et al., Ann. Rep. Med. Chem., 1996, 31, 289-298) and activating transcription factors (such as ATF-2, MAX, CHOP and C/ERPb) as well as other kinases (such as MAPKAP-K2/3 or MK2/3), and are themselves activated by physical and chemical stress (e.g. UV, osmotic stress), pro-inflammatory cytokines and bacterial lipopolysaccharide (LPS) (Herlaar E. & Brown Z., Molecular Medicine Today, 1999, 5, 439-447). The products of p38 phosphorylation have been shown to mediate the production of inflammatory cytokines, including tumor necrosis factor alpha (TNF α) and interleukin- (IL-)-1, and cyclooxygenase-2 (COX-2). IL-1 and TNFα are also known to stimulate the production of other proinflammatory cytokines such as IL-6 and IL-8.

IL-1 and TNFα are biological substances produced by a variety of cells, such as monocytes or macrophages. IL-1 has been demonstrated to mediate a variety of biological activities thought to be important in immunoregulation and other physiological conditions such as inflammation (e.g. Dinarello et al., Rev. Infect. Disease, 1984, 6, 51). Excessive or unregulated TNF production (particularly TNFα) has been implicated in mediating or exacerbating a number of diseases, and it is believed that TNF can cause or contribute to the effects of inflammation in general. IL-8 is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes and basophils. Increase in IL-8 production is also responsible for chemotaxis of neutrophils into the inflammatory site in vivo.

Inhibition of signal transduction via p38, which in addition to IL-1, TNF and IL-8 described above is also required for the synthesis and/or action of several additional pro-inflammatory proteins (e.g., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for p38 kinase inhibitors (Badger et al., J. Pharm. Exp. Thera., 1996, 279, 1453-1461; Griswold et al, Pharmacol. Comm., 1996, 7, 323-229). In particular, p38 kinase inhibitors have been described as potential agents for treating rheumatoid arthritis. In addition to the links between p38 activation and chronic inflammation and arthritis, there is also data implicating a role for p38 in the pathogenesis of airway diseases in particular COPD and asthma. Stress stimuli (including tobacco smoke, infections or oxidative products) can cause inflammation within the lung environment. Inhibitors of p38 have been shown to inhibit LPS and ovalbumin induced airway TNF-α IL-1β, IL-6, IL-4, IL-5 and IL-13 (Haddad et al, Br. J. Pharmacol., 2001, 132 (8), 1715-1724; Underwood et al, Am. J. Physiol. Lung Cell. Mol. 2000, 279, 895-902; Duan et al., 2005 Am. J. Respir. Cult. Care Med., 171, 571-578; Escott et al Br. J. Pharmacol., 2000, 131, 173-176; Underwood et al., J. Pharmacol. Exp. Ther. 2000, 293, 281-288). Furthermore, they significantly inhibit neutrophilia and the release of MMP-9 in LPS, ozone or cigarette smoke animal models. There is also a significant body of preclinical data highlighting the potential benefits of inhibition of the p38 kinase that could be relevant in the lung (Lee et al., Immunopharmacology, 2000, 47, 185-200). Thus, therapeutic inhibition of p38 activation may be important in the regulation of airway inflammation.

The implication of the p38MAPK pathway in various diseases has been reviewed by P. Chopra et al. (Expert Opinion on Investigational Drugs, 2008, 17(10), 1411-1425). It is believed that the compounds of the present invention can be used to treat p38 mediated diseases such as: asthma, chronic or acute bronchoconstriction, bronchitis, acute lung injury and bronchiectasis, pulmonary artery hypertension, tuberculosis, lung cancer, inflammation generally (e.g. inflammatory bowel disease), arthritis, neuroinflammation, pain, fever, fibrotic diseases, pulmonary disorders and diseases (e.g., hyperoxic alveolar injury), cardiovascular diseases, post-ischemic reperfusion injury and congestive heart failure, cardiomyopathy, stroke, ischemia, reperfusion injury, renal reperfusion injury, brain edema, neurotrauma and brain trauma, neurodegenerative disorders, central nervous system disorders, liver disease and nephritis, gastrointestinal conditions, ulcerative diseases, Crohn's disease, ophthalmic diseases, ophthalmological conditions, glaucoma, acute injury to the eye tissue and ocular traumas, diabetes, diabetic nephropathy, skin-related conditions, myalgias due to infection, influenza, endotoxic shock, toxic shock syndrome, autoimmune disease, graft rejection, bone resorption diseases, multiple sclerosis, psoriasis, eczema, disorders of the female reproductive system, pathological (but non-malignant) conditions, such as hemaginomas, angiofibroma of the nasopharynx, and avascular necrosis of bone, benign and malignant tumors/neoplasia including cancer, leukaemia, lymphoma, systemic lupus erthrematosis (SLE), angiogenesis including neoplasia, haemorrhage, coagulation, radiation damage, and/or metastasis. Chronic release of active TNF can cause cachexia and anorexia, and TNF can be lethal. TNF has also been implicated in infectious diseases. These include, for example, malaria, mycobacterial infection and meningitis. These also include viral infections, such as HIV, influenza virus, and herpes virus, including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV7), human herpesvirus-8 (HHV-8), pseudorabies and rhinotracheitis, among others.

Known P38 kinase inhibitors have been reviewed by G. J. Hanson (Expert Opinions on Therapeutic Patents, 1997, 7, 729-733) J Hynes et al. (Current Topics in Medicinal Chemistry, 2005, 5, 967-985), C. Dominguez et al (Expert Opinions on Therapeutics Patents, 2005, 15, 801-816) and L. H. Pettus & R. P. Wurtz (Current Topics in Medicinal Chemistry, 2008, 8, 1452-1467). P38 kinase inhibitors containing a triazolopyridine motif are known in the art, for example WO07/091, 152, WO04/072072, WO06/018727.

SUMMARY OF THE INVENTION

The compounds of the present invention are inhibitors of p38 mitogen activated protein kinase ("p38 MAPK", "p38 kinase" or "p38"), including p38α kinase, and are inhibitors of cytokine and chemokine production including TNFα and IL-8 production. They have a number of therapeutic applications, in the treatment of inflammatory diseases, particularly allergic and non-allergic airways diseases, more particularly obstructive or inflammatory airways diseases such as chronic obstructive pulmonary disease ("COPD") and asthma. They are therefore particularly suited for pulmonary delivery, by inhalation by nose or mouth.

According to the invention there is provided a compound of formula (I), or a pharmaceutically acceptable salt thereof:

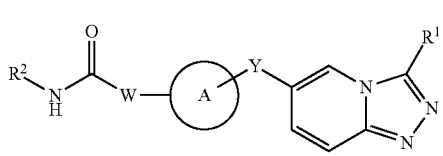

(I)

wherein;
$R^1$ is $C_1$-$C_6$ alkyl, $C_3$-$C_6$ cycloalkyl, phenyl which is optionally substituted, 5- or 6-membered monocyclic heteroaryl which is optionally substituted or a radical of formula (II)

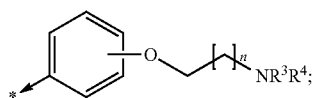

(II)

wherein n is 1 or 2; and $R^3$ and $R^4$ are independently H or $C_1$-$C_6$ alkyl, or $R^3$ and $R^4$ taken together with the nitrogen to which they are attached form a 6-membered heterocyclic ring optionally containing a further heteroatom selected from N and O;

Y is —O— or —S(O)$_p$— wherein p is 0, 1 or 2;

A is an optionally substituted divalent arylene radical, or a mono- or bicyclic heteroarylene radical, or a $C_3$-$C_6$ divalent cycloalkylene radical having 5 or 6 ring atoms, or a piperidinylene radical wherein the ring nitrogen is linked to $R^2$NHC(=O)W—;

W is a bond, —NH— or —C($R^A$)($R^B$)—, wherein $R^A$ and $R^B$ are independently H, methyl, ethyl, amino, hydroxyl or halo; and $R^2$ is a radical of formula (IIIA), (IIIB) or (IIIC):

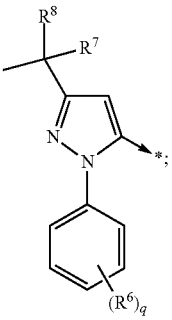

(IIIA)

(IIIB)

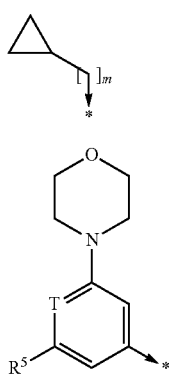

-continued

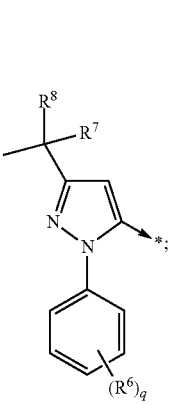

(IIIC)

wherein
m is 0 or 1;
q is 0, 1, 2 or 3;
T is —N= or —CH=;
$R^5$ is H or F;
$R^7$ is —CH$_3$, —C$_2$H$_5$, —CH$_2$OH, —CH$_2$SCH$_3$, —SCH$_3$ or —SC$_2$H$_5$;
$R^8$ is —CH$_3$ or —C$_2$H$_5$; and
each occurrence of $R^6$ is independently H, $C_1$-$C_6$ alkyl, hydroxy or halo; or a single occurrence of $R^6$ is a radical of formula (IVA), (IVB) or (IVC)

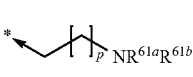

(IVA)

(IVB)

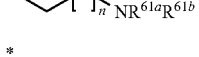

(IVC)

while any other occurrence of $R^6$ is independently H, $C_1$-$C_6$ alkyl, hydroxyl or halo;
wherein n and p are as defined above;
and wherein in $R^6$
$R^{61a}$ and $R^{61b}$ are H, alkyl, or $R^{61a}$ and $R^{61b}$ may be joined together with the nitrogen to which they are attached to form a heterocyclic ring optionally containing a further heteroatom selected from N and O.

In another aspect, the invention includes pharmaceutical compositions comprising a compound of the invention, together with one or more pharmaceutically acceptable carriers and/or excipients. Particularly preferred are compositions adapted for inhalation for pulmonary administration.

In another aspect, the invention includes the use of a compound of the invention for the treatment of diseases or conditions which benefit from inhibition of p38 MAP kinase activity. The treatment of obstructive or inflammatory airways diseases is a preferred use. All forms of obstructive or inflammatory airways diseases are potentially treatable with the compounds of the present invention, in particular an obstructive or inflammatory airways disease that is a member selected from the group consisting of chronic eosinophilic pneumonia, asthma, COPD, COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, chronic inflammatory diseases including cystic fibrosis, broncietasis and pulmonary fibrosis (Idiopathic). Efficacy is anticipated when p38 kinase inhibitors are administered either locally to the lung (for example by inhalation and intranasal delivery) or via systemic routes (for example, oral, intravenous and subcutaneous delivery).

DESCRIPTION OF THE INVENTION

Terminology

As used herein, the term "$(C_a\text{-}C_b)$alkyl" wherein a and b are integers, refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein, the term "carbocyclic" refers to a mono-, bi- or tricyclic radical having up to 16 ring atoms, all of which are carbon, and includes aryl and cycloalkyl.

As used herein, the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

The term "divalent cycloalkylene radical" refers to a cycloalkyl radical having two unsatisfied valencies such as 1,3-cyclopentylene and 1,4-cyclohexylene, as follows:

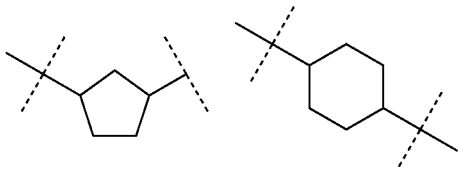

As used herein, the unqualified term "aryl" refers to a mono- or bi-cyclic carbocyclic aromatic radical, and includes radicals having two monocyclic carbocyclic aromatic rings which are directly linked by a covalent bond. Illustrative of such radicals are phenyl, biphenyl and napthyl.

The term "divalent arylene radical" refers to a monocyclic or bicyclic aryl radical having two unsatisfied valencies such as 1,3-phenylene or 1,4-phenylene as follows:

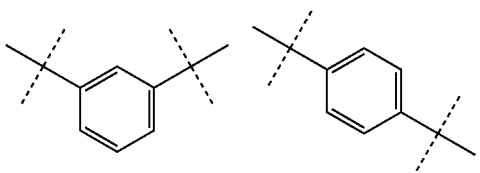

or 1,4-naphthalenyl as follows:

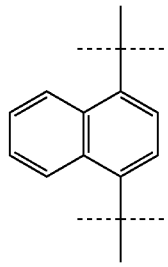

As used herein, the unqualified term "heteroaryl" refers to a mono- or bi-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative examples of such radicals are thienyl, benzothienyl, furyl, benzofuryl, pyrrolyl, imidazolyl, benzimidazolyl, thiazolyl, benzothiazolyl, isothiazolyl, benzisothiazolyl, pyrazolyl, oxazolyl, benzoxazolyl, isoxazolyl, benzisoxazolyl, isothiazolyl, triazolyl, benzotriazolyl, thiadiazolyl, oxadiazolyl, pyridinyl, pyridazinyl, pyrimidinyl, pyrazinyl, triazinyl, indolyl and indazolyl.

As used herein, the unqualified term "heterocyclyl" or "heterocyclic" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzofuranyl, pyranyl, isoxazolyl, benzimidazolyl, methylenedioxyphenyl, ethylenedioxyphenyl, maleimido and succinimido groups.

The term "divalent heteroarylene radical" refers to a monocyclic or bicyclic heteroaryl radical having two unsatisfied valencies such as the following:

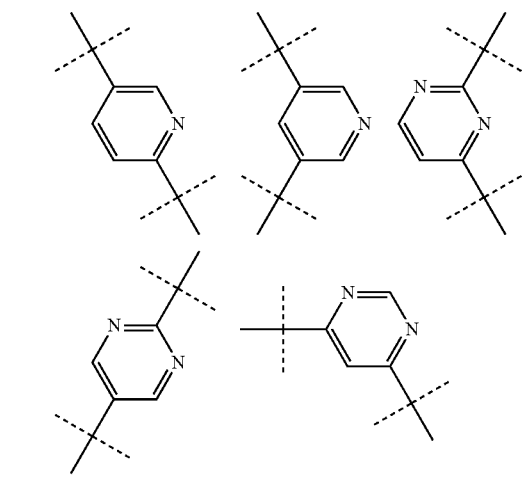

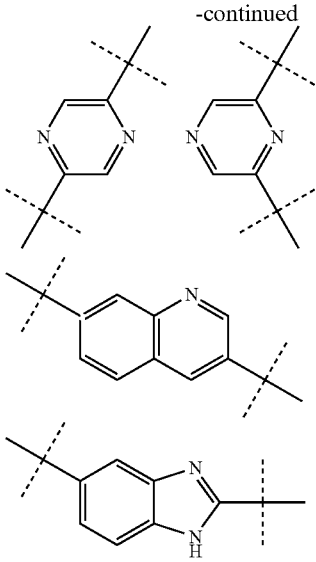

with the following being currently preferred

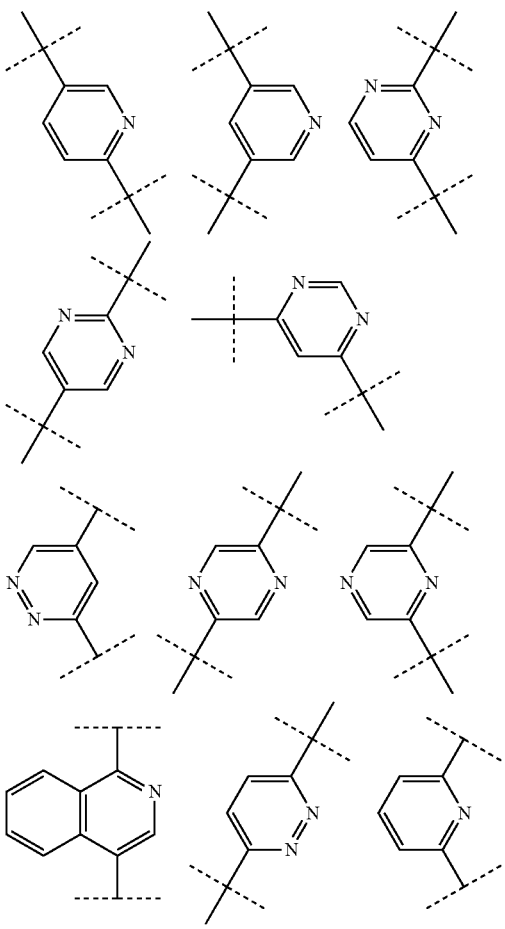

Unless otherwise specified in the context in which it occurs, the term "substituted" as applied to any aryl or heteroaryl moiety herein means substituted with at least one substituent, for example selected from ($C_1$-$C_6$)alkyl, ($C_1$-$C_6$)fluoroalkyl, ($C_1$-$C_6$)alkoxy (including methylenedioxy and ethylenedioxy substitution on adjacent carbon atoms of an aromatic ring), ($C_1$-$C_6$)fluoroalkoxy, ($C_1$-$C_6$)alkoxy-($C_1$-$C_6$)alkyl, benzyloxy-($C_1$-$C_6$)alkyl, ($C_1$-$C_6$)alkoxy-($C_1$-$C_6$)alkoxy, benzyloxy-($C_1$-$C_6$)alkoxy, hydroxy, hydroxy($C_1$-$C_6$)alkyl, hydroxy($C_1$-$C_6$)alkoxy, mercapto, mercapto($C_1$-$C_6$)alkyl, ($C_1$-$C_6$)alkylthio, cyclopropyl, halo (including fluoro and chloro), O-benzyl, nitro, nitrile (cyano), —COOH, tetrazolyl, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NRACONR$^A$R$^B$ wherein R$^A$ and R$^B$ are independently a ($C_1$-$C_4$)alkyl group, or R$^A$ and R$^B$ when attached to the same nitrogen may form, together with that nitrogen, a cyclic amino group such as a morpholinyl, piperidinyl or piperazinyl group. An "optional substituent" may be one of the substituent groups encompassed in the above description.

Compounds of the invention may exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers may be prepared by the application of adaptation of known methods (e.g. asymmetric synthesis).

As used herein the term "salt" includes base addition, acid addition and ammonium salts. As briefly mentioned above compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)aminomethane, L-arginine, L-lysine, N-ethyl piperidine, dibenzylamine and the like. Those compounds of the invention which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, trifluoroacetic, tartaric, succinic, fumaric, maleic, malic, salicylic, citric, methanesulphonic, p-toluenesulphonic, benzoic, benzenesulfonic, glutamic, lactic, and mandelic acids and the like. Those compounds (I) which have a basic nitrogen can also form quaternary ammonium salts with a pharmaceutically acceptable counter-ion such as ammonium, chloride, bromide, acetate, formate, p-toluenesulfonate, succinate, hemi-succinate, naphthalene-bis sulfonate, methanesulfonate, trifluoroacetate, xinafoate, and the like. For a review on salts, see *Handbook of Pharmaceutical Salts: Properties, Selection, and Use* by Stahl and Wermuth (Wiley-VCH, Weinheim, Germany, 2002).

It is expected that compounds of the invention may be prepared in the form of hydrates, and solvates. Any reference herein, including the claims herein, to "compounds with which the invention is concerned" or "compounds of the invention" or "the present compounds", and the like, includes reference to salts hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in several polymorphic forms and may be obtained in different crystal habits.

The compounds may also be administered in the form of prodrugs thereof. Thus certain derivatives of the compounds which may be active in their own right or may have little or no pharmacological activity themselves can, when administered into or onto the body, be converted into compounds of the invention having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and V. J. Stella) and *Bioreversible Carriers in Drug Design*, Pergamon Press, 1987 (ed. E. B. Roche, American Pharmaceutical Association; C. S. Larsen and J. Østergaard, Design and application of prodrugs, In Textbook of Drug Design and Discovery, 3$^{rd}$ Edition, 2002, Taylor and Francis).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985). Such examples could be a prodrug of a carboxyl group (such as —CO—O—CH$_2$—O—CO-tBu as used in the pivampicillin prodrug of ampicillin), an amide (—CO—NH—CH$_2$—NAlk$_2$) or an amidine (—C(=N—O—CH$_3$)—NH$_2$).

In the compounds of the invention, the divalent radical —W-[A]-Y— may be, for example, any of the corresponding radicals in the specific Example compounds below. For example, that radical may be one of the following formulae (B)-(J):

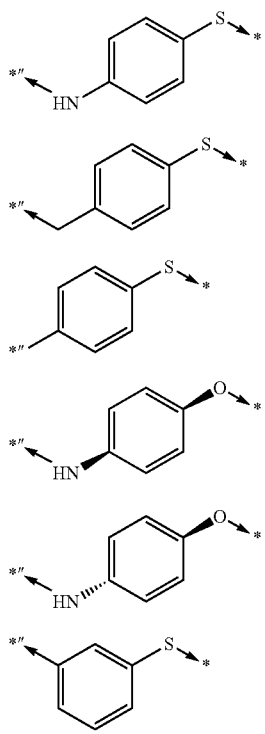

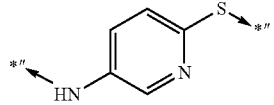

(H)

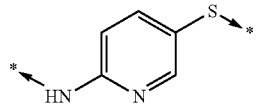

(I)

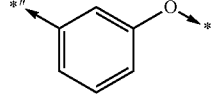

(J)

One subclass of compounds of the invention has formula (IA):

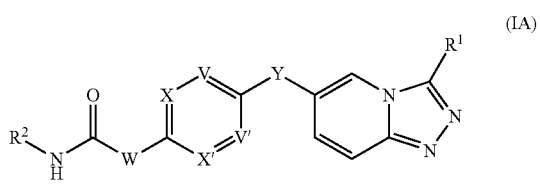

(IA)

wherein V, V', X and X' are independently —CH= or —N=; and R$^1$, R$^2$, Y and W are as defined in relation to formula (I). Within this subclass, compounds may have formula (IA$^1$):

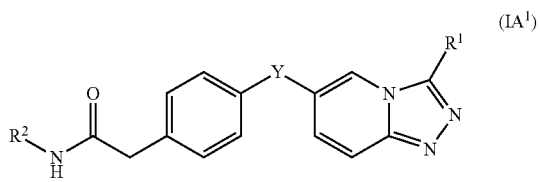

(IA$^1$)

wherein Y is O or S and R$^1$ and R$^2$ are as defined in relation to formula (I).

Another subclass of compounds of the invention has formula (IB):

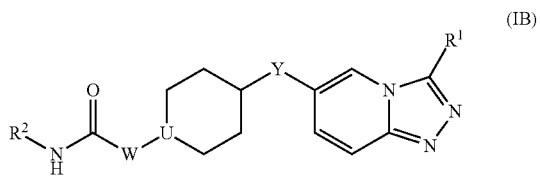

(IB)

wherein U is CH or N, and R$^1$, R$^2$, Y and W are as defined in relation to formula (I), with the proviso that when U is N then W is not NH. Within this subclass, compounds may have formula (IB$^1$):

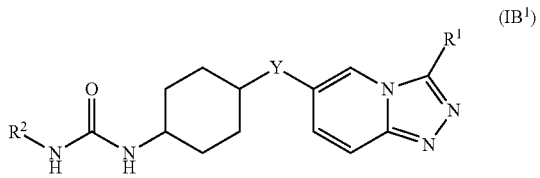
(IB¹)

wherein Y is O or S and $R^1$ and $R^2$ are as defined in relation to formula (I).

A further subclass of compounds of the invention has formula (IC):

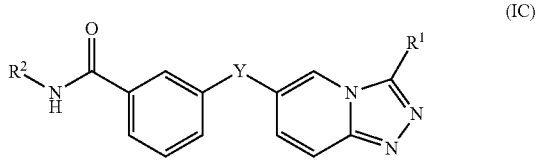
(IC)

wherein Y is O or S, $R^2$ is as defined in claim 1, and $R^1$ is phenyl, 5- or 6-membered monocyclic heteroaryl or a radical of formula (II) as defined in relation to formula (I) above.

In the compounds of the invention, including the subclasses of formulae (IA), (IA¹), (IB), (IB¹), and (IC) above, specific currently preferred structural features include the following:

$R^1$ may be a group of formula (II) as defined in relation to formula (I) above wherein the group —$NR^3R^4$ is morpholinyl.

$R^1$ may be isopropyl or 2,6-dichlorophenyl.

$R^2$ may be a radical of formula (IIIC) as defined in relation to formula (I) above, wherein $R^7$ and $R^8$ are each methyl.

$R^2$ may have formula (IIID), (IIIE), (IIIF) or (IIIG):

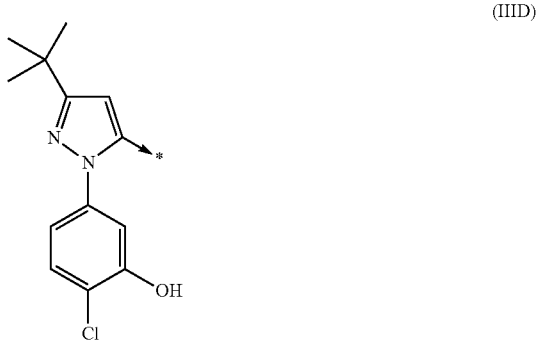
(IIID)

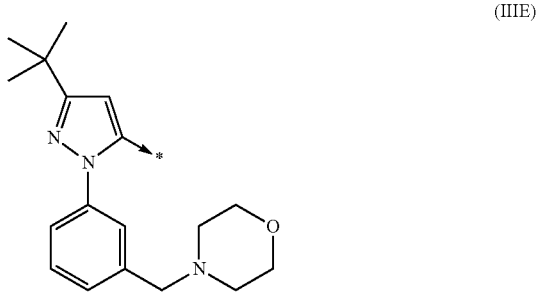
(IIIE)

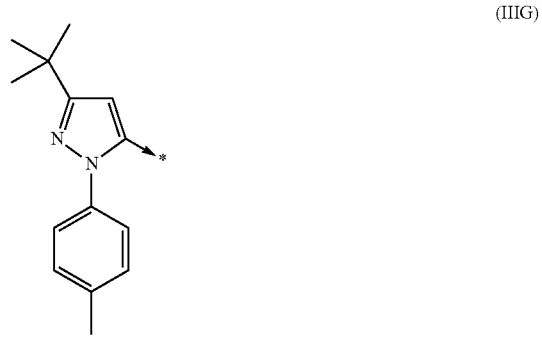
(IIIF)

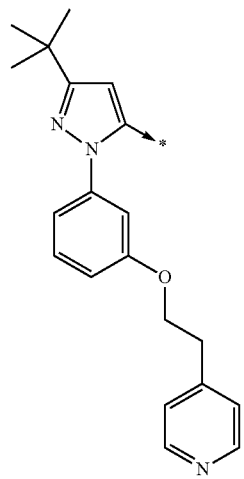
(IIIG)

$R^2$ may be a radical of formula (IIIA) as defined in relation to formula (I), wherein m is 0.

$R^2$ may be a radical of formula (IIIB) as defined in relation to formula (I) above, wherein (a) T is —CH═ and $R^5$═H; or (b) T is —N═ and $R^5$═H; or (c) T-CH═ and $R^5$═F.

Optional substituents in the divalent radical A include —CN, —F, —Cl, —Br, —NO₂, —OH, —SO₂$C_1$-$C_2$ alkyl, —SO₂$C_1$-$C_2$ fully or partially fluorinated alkyl, $C_1$-$C_4$ alkyl, fully or partially fluorinated $C_1$-$C_4$ alkyl, $C_1$-$C_4$ alkoxy, fully or partially fluorinated $C_1$-$C_4$ alkoxy, and —SCF₃.

The divalent radical A may be a six-membered ring such as phenylene or pyridinylene, linked to Y and W in a 1,3 (meta) or 1,4 (para) orientation.

The divalent radical A may be a cyclohexylene radical linked to W and Y in a trans-1,4 orientation.

W may be —CH₂—.

Utility

As mentioned above the compounds of the invention are p38MAPK inhibitors, and thus may have utility for the treatment of diseases or conditions which benefit from inhibition of the p38 enzyme. Such diseases and conditions are known from the literature and several have been mentioned above. However, the compounds are generally of use as anti-inflammatory agents, particularly for use in the treatment of respiratory disease. In particular, the compounds may be used in the treatment of chronic obstructive pulmonary disease (COPD), chronic bronchitis, lung fibrosis, pneumonia, acute respiratory distress syndrome (ARDS), pulmonary emphysema, or smoking-induced emphysema, intrinsic (non-allergic asthma and extrinsic (allergic) asthma, mild asthma, moderate asthma, severe asthma, steroid resistant asthma, neutrophilic asthma, bronchitic asthma, exercise induced asthma, occupational asthma and asthma induced following bacterial infection, cystic fibrosis, pulmonary fibrosis and bronchiectasis.

Compositions

As mentioned above, the compounds with which the invention is concerned are p38 kinase inhibitors, and are useful in the treatment of several diseases for example inflammatory diseases of the respiratory tract. Examples of such diseases are referred to above, and include asthma, rhinitis, allergic airway syndrome, bronchitis and chronic obstructive pulmonary disease.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 μg to about 1 mg per kg body weight of a human, preferably 0.1 μg to 50 μg per kg, in single or divided doses. On the other hand, it may be necessary to use dosages outside these limits in some cases. For the purpose of the invention, inhaled administration is preferred.

The compounds with which the invention is concerned may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

However, for treatment of an inflammatory disease of the respiratory tract, compounds of the invention may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronisation. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

By way of example, a composition of the invention may be prepared as a suspension for delivery from a nebuliser or as an aerosol in a liquid propellant, for example for use in a pressurised metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane)

In a preferred embodiment of the invention, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 μm.

In the case of an aerosol-based formulation, an example is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321). Additionally, compounds of the invention may be delivered in multi-chamber devices thus allowing for delivery of combination agents.

Combinations

Other compounds may be combined with compounds with which the invention is concerned for the prevention and treatment of inflammatory diseases, in particular respiratory diseases. Thus the present invention is also concerned with pharmaceutical compositions comprising a therapeutically effective amount of a compound of the invention and one or more other therapeutic agents. Suitable therapeutic agents for a combination therapy with compounds of the invention include, but are not limited to: (1) corticosteroids, such as fluticasone propionate, fluticasone furoate, mometasone furoate, beclometasone dipropionate, ciclesonide, budesonide, GSK 685698, GSK 870086, QAE 397, QMF 149, TPI-1020; (2) β2-adrenoreceptor agonists such as salbutamol, albuterol, terbutaline, fenoterol, and long acting β2-adrenoreceptor agonists such as salmeterol, indacaterol, formoterol (including formoterol fumarate), arformoterol, carmoterol, GSK 642444, GSK 159797, GSK 159802, GSK 597501, GSK 678007, AZD3199; (3) corticosteroid/long acting β2 agonist combination products such as salmeterol/fluticasone propionate (Advair/Seretide), formoterol/budesonide (Symbicort), formoterol/fluticasone propionate (Flutiform), formoterol/ciclesonide, formoterol/mometasone furoate, indacaterol/mometasone furoate, Indacaterol/QAE 397, GSK 159797/GSK 685698, GSK 159802/GSK 685698, GSK 642444/GSK 685698, GSK 159797/GSK 870086, GSK 159802/GSK 870086, GSK 642444/GSK 870086, arformoterol/ciclesonide; (4) anticholinergic agents, for example muscarinic-3 (M3) receptor antagonists such as ipratropium bromide, tiotropium bromide, Aclidinium (LAS-34273), NVA-237, GSK 233705, Darotropium, GSK 573719, GSK 961081, QAT 370, QAX 028; (5) dual pharmacology M3-anticholinergic/β2-adrenoreceptor agonists such as GSK961081; (6) leukotriene modulators, for example leukotriene antagonists such as montelukast, zafirulast or pranlukast or leukotriene biosynthesis inhibitors such as Zileuton or BAY-1005, or LTB4 antagonists such as Amelubant, or FLAP inhibitors such as GSK 2190914, AM-103; (7) phosphodiesterase-IV (PDE-IV) inhibitors (oral or inhaled), such as roflumilast, cilomilast, Oglemilast, ONO-6126, Tetomilast, Tofimilast, UK 500,001, GSK 256066; (8) antihistamines, for example selective histamine-1 (H1) receptor antagonists, such as fexofenadine, citirizine, loratidine or astemizole or dual H1/H3 receptor antagonists such as GSK 835726, GSK 1004723; (9) antitussive agents, such as codeine or dextramorphan; (10) a mucolytic, for example N acetyl cysteine or fudostein; (11) a expectorant/mucokinetic modulator, for example ambroxol, hypertonic solutions (e.g. saline or mannitol) or surfactant; (12) a peptide mucolytic, for example recombinant human deoxyribonoclease I (dornase-alfa and rhDNase) or helicidin; (13) antibiotics, for example azithromycin, tobramycin and aztreonam; (14) non-selective COX-1/COX-2 inhibitors, such as ibuprofen or ketoprofen; (15) COX-2 inhibitors, such as celecoxib and rofecoxib; (16) VLA-4 antagonists, such as those described in WO97/03094 and WO97/02289; (17) TACE inhibitors and TNF-α inhibitors, for example anti-TNF monoclonal antibodies, such as Remicade and CDP-870 and TNF receptor immunoglobulin molecules, such as Enbrel; (18) inhibitors of matrix metalloprotease, for example MMP-12; (19) human neutrophil elastase inhibitors, such as ONO-6818 or those described in WO2005/026124, WO2003/053930 and WO06/082412; (20) A2b antagonists such as those described in WO2002/42298; (21) modulators of chemokine receptor function, for example antagonists of CCR3 and CCR8; (22) compounds which modulate the action of other prostanoid receptors, for example a thromboxane $A_2$ antagonist; DP1 antagonists such as MK-0524, CRTH2 antagonists such as ODC9101 and AZD1981 and mixed DPI/CRTH2 antagonists such as AMG 009; (23) PPAR agonists including PPAR alpha agonists (such as fenofibrate), PPAR delta agonists, PPAR gamma agonists such as Pioglitazone, Rosiglitazone and Balaglitazone; (24) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (25) A2a agonists such as those described in EP1052264 and EP1241176; (26) CXCR2 or IL-8 antagonists such as SCH 527123 or GSK 656933; (27) IL-R signalling modulators such as kineret and ACZ 885; (28) MCP-1 antagonists such as ABN-912.

Methods of Synthesis

Compounds of the invention may be prepared according to the routes illustrated in Schemes 1-6.

Scheme 1

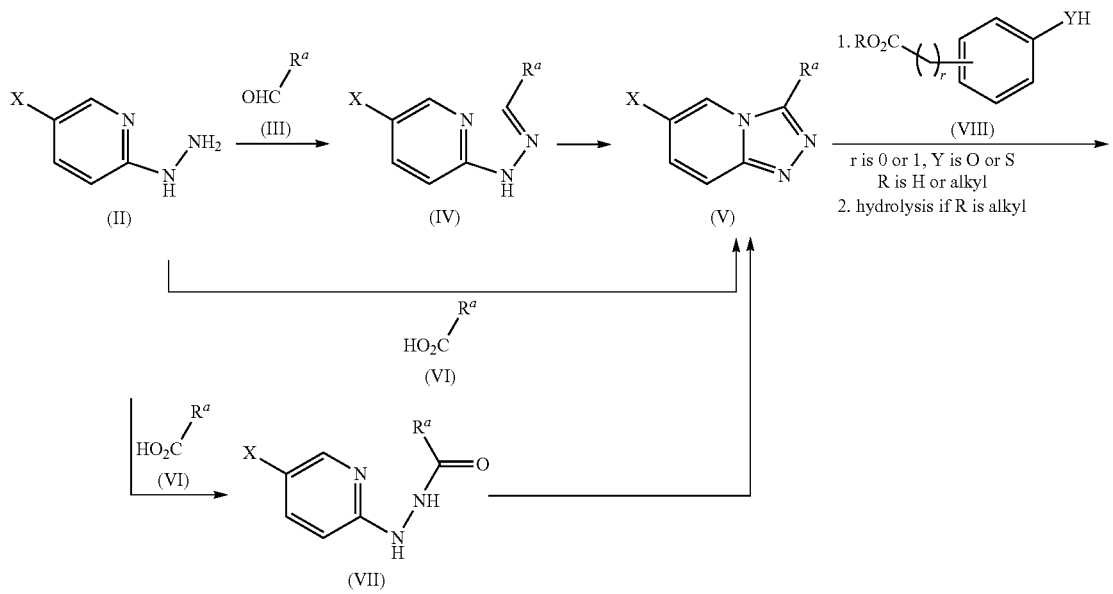

-continued

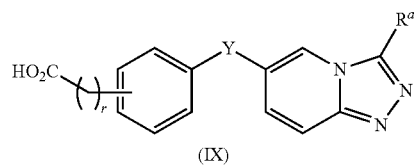
(IX)

(X)

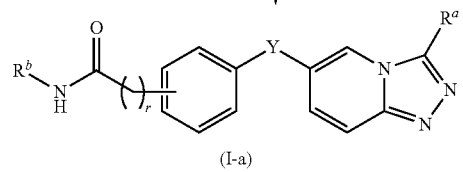
(I-a)

Compounds of general formula (I-a) may be prepared from compounds of general formula (IX):

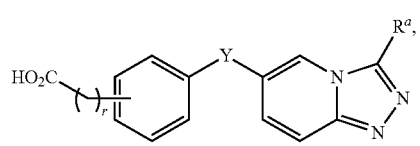
(IX)

wherein r is 0 or 1, Y is S or O, and $R^a$ is as defined for $R^1$ in general formula (I). by reaction with an amine of general formula (X):

$R^b NH_2$ (X), wherein $R^b$ is as defined for $R^2$ in general formula (I).

Using a suitable coupling agent such as 2-(7-aza-1H-benzotriazole-1-yl)-1,1,3,3-tetramethyluronium hexafluorophosphate, 1-ethyl-3-(3'-dimethylaminopropyl)carbodiimide or dicyclohexylcarbodiimide in the presence of a base such as diisopropylethylamine or triethylamine. The reaction may take place in a suitable solvent such as dichloromethane, N,N-dimethylformamide or tetrahydrofuran at a range of temperatures, preferably at room temperature.

Alternatively, compounds of formula (I-a) may be prepared from compounds of general formula (IX) by reaction with a suitable halogenating agent which as oxalyl chloride or thionyl chloride in the absence or presence of a solvent such as dichloromethane or N,N-dimethylformamide at a range of temperatures, preferably from room temperature to 100° C., followed by reaction with an amine of general formula (X), using a suitable base such as diisopropylethylamine, in a suitable solvent such as tetrahydrofuran at a range of temperatures, preferably from room temperature to 80° C.

Compounds of general formula (IX) may be prepared from compounds of general formula (V):

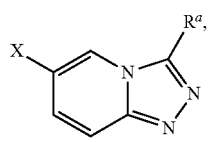
(V)

wherein X is a suitable leaving group such as fluorine, bromide or iodide, by reaction with a compound of general formula (VIII):

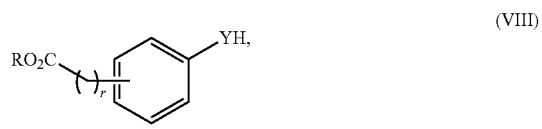
(VIII)

wherein R is H or alkyl, using a suitable calatyst such as copper (I) iodide, copper (I) chloride, palladium acetate, tetrakis(triphenylphosphine)palladium (0) or dichloro(1,1'-bis(diphenylphosphino)ferrocene)palladium (II), in the absence or the presence of a suitable ligand such as (2,9-dimethyl)-1,10-phenanthroline, proline, 1,2-cyclohexyldiamine or a phosphine, using a base such as cesium carbonate, potassium hydroxide, potassium carbonate or sodium tert-butoxide. The reaction may take place in a suitable solvent such as toluene, N-methylpyrrolidinone or N,N-dimethylformamide at a range of temperatures, preferably between 40 and 150° C.; followed, if R is alkyl, by hydrolysis according to methods known to those skilled in the art.

Compounds of general formula (V) may be prepared from compounds of general formula (IV):

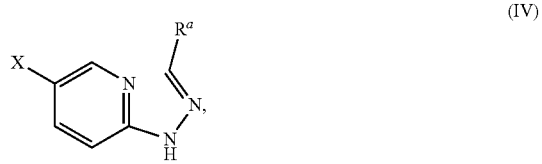
(IV)

using a suitable oxidant such as chloramine T, lead tetracetate or phenyliodine(III)diacetate, in a suitable solvent such as dichloromethane or ethanol at a range of temperatures, preferably between room temperature and 100° C.

Compounds of general formula (IV) may be prepared from compounds of general formula (II):

$$\text{(II)}$$

by reaction with an aldehyde of general formula (III):

$$R^a\text{CHO} \quad \text{(III)},$$

in a suitable solvent such as ethanol or tetrahydrofuran at a range of temperatures, preferably between room temperature and 80° C.

Alternatively, compounds of formula (IV) may be prepared from compounds of formula (II) by reaction with a compound of general formula (VI):

$$R^a\text{CO}_2\text{H} \quad \text{(VI)},$$

using a suitable acylating/dehydrating agent such as triphenylphosphine/trichloroacetonitrile in the presence of a base such as diisopropylethylamine, in a suitable solvent such as dichloromethane or acetonitrile, at a range of temperatures, preferably between room temperature and 150° C.

Alternatively, compounds of formula (IV) may be prepared from compounds of formula (VII):

$$\text{(VII)}$$

using a suitable dehydrating agent such as Burgess' reagent, triphenyl phosphine and hexachloroethane, phosphorus oxychloride, acetic acid or Mitsunobu conditions (diethylazodicarboxylate/triphenylphosphine/trimethylsilylazide), in the absence or presence of a suitable solvent such as tetrahydrofuran, toluene or NMP, at a range of temperatures, preferably between room temperature and 120° C.

Compounds of general formula (VII) may be prepared from compounds of general formula (II) by reaction with a carboxylic acid of general formula (VI), as described for the preparation of compounds of formula (I-a) from compounds of formula (IX).

Scheme 2

Compounds of general formula (I-b) may be prepared from compounds of general formula (XII):

(XII), wherein $R^a$ is as defined for $R^1$ in general formula (I), by reaction with a compound of general formula (XIII):

$$\text{(XIII)}$$

wherein $R^b$ is as defined for $R^2$ in general formula (I), in a suitable solvent such as dimethyl sulfoxide, 1,4-dioxane or acetonitrile, in the presence of a base such as diisopropylethylamine at a range of temperatures, preferably between room temperature and 100° C.

Compounds of general formula (XIII) may be prepared from amines of general formula (X) according to known literature procedures (e.g. WO2006/009741, EP1609789).

Alternatively compounds of general formula (I-b) may be prepared from compounds of general formula (XII) by reaction with an amine of general formula (X), using a suitable coupling agent such as phosgene, diphosgene or triphosgene, in a suitable solvent such as dichloromethane, toluene, tetrahydrofuran or acetonitrile, using a suitable base such as triethylamine, pyridine or diisopropylethylamine, at a range of temperatures preferably between 0 and 100° C.

Compounds of general formula (XII) may be prepared from compounds of general formula (V):

by reaction with a compound of general formula (XI):

(XI)

H₂N—C₆H₄—SH, using a suitable base such as cesium carbonate, potassium hydroxide, potassium carbonate or sodium tert-butoxide, in the absence or presence of a suitable calatyst such as copper (I) iodide or copper (I) bromide and a suitable ligand such as (2,9-dimethyl)-1,10-phenanthroline, proline or 1,2-cyclohexyldiamine. The reaction may take place in a suitable solvent such as toluene, N-methylpyrrolidinone, methanol or N,N-dimethylformamide at a range of temperatures, preferably between 40 and 150° C.

Scheme 3

(V) + (XIV) → (XV) → (XVI)

(X) → (XIII) →

Compounds of general formula (I-c) may be prepared from compounds of general formula (XVI):

(XVI)

by reaction with a compound of general formula (XIII) or (X), as described for the preparation of compounds of formula (I-b) from compounds of formula (XII).

Compounds of general formula (XVI) may be prepared from compounds of general formula (XV):

(XV)

wherein $R^c$ may be a suitable protecting group or H by deprotection according to methods known to those skilled in the art.

Compounds of general formula (XV) may be prepared from compounds of general formula (V):

(V)

by reaction with a compound of general formula (XIV):

(XIV)

$R^c$HN—C₆H₁₀—OH, as described for the preparation of compounds of formula (XII) from compounds of formula (XI).

Scheme 4

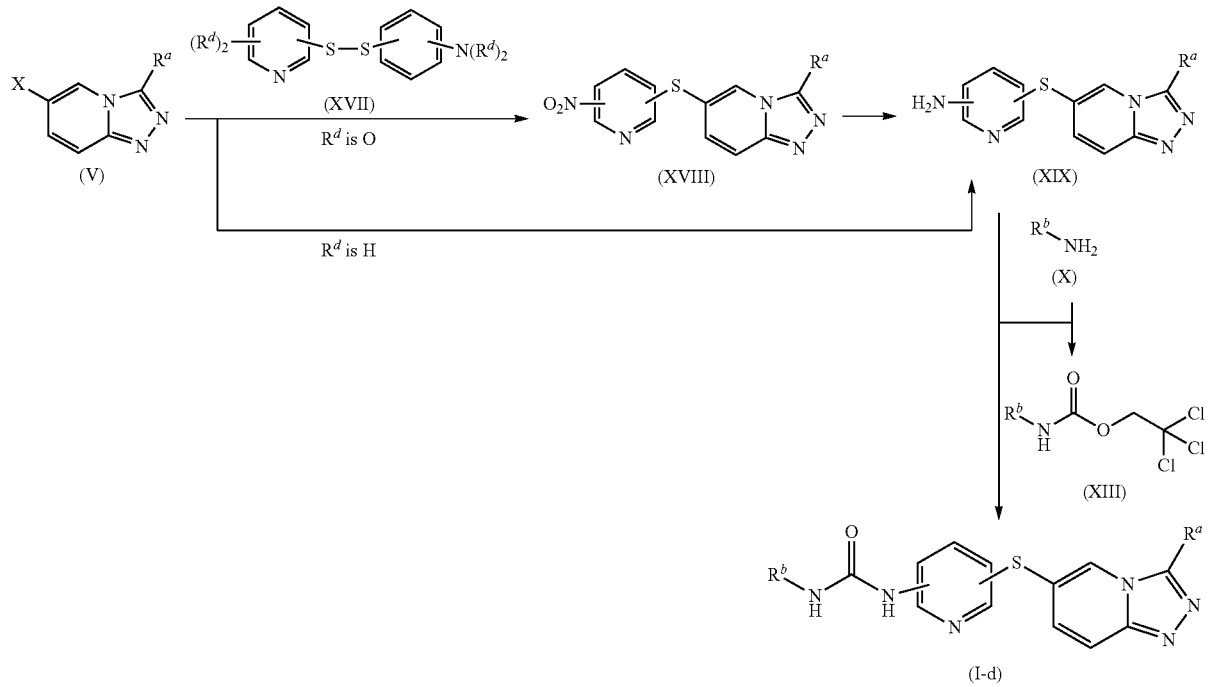

Compounds of general formula (I-d) may be prepared from compounds of general formula (XIX):

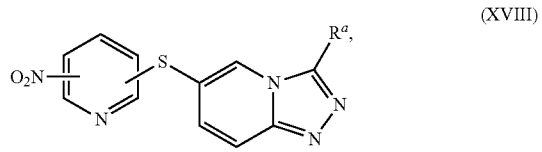
(XIX)

by reaction with a compound of general formula (XIII) or (X), as described for the preparation of compounds of formula (I-b) from compounds of formula (XII).

Compounds of general formula (XIX) may be prepared from compounds of general formula (XVIII):

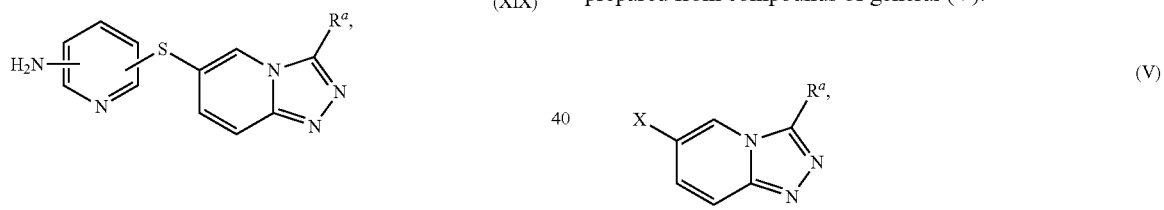

by reaction with a suitable reductive agent such as tin (II) chloride, iron or hydrogen gas in the presence of a catalyst such as palladium on charcoal, platinum oxide or Raney Nickel, in the presence or absence of acid such as hydrogen chloride or acetic acid, in a suitable solvent such as methanol, ethanol or ethyl acetate, at a range of temperatures, preferably between room temperature and 80° C.

Alternatively compounds of general formula (XIX) may be prepared from compounds of general (V):

(V)

by reaction with a compound of general formula (XVII):

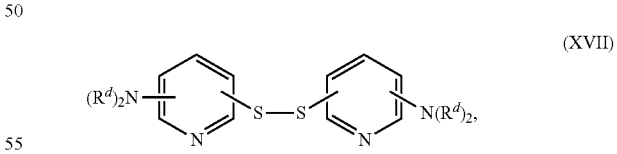

wherein $R^d$ is H, with a suitable metallated species such as butyllithium, magnesium or i-propylmagnesium chloride, in a suitable solvent such as tetrahydrofuran or diethyl ether, at a range of temperatures, preferably between −78° C. and room temperature.

Compounds of general formula (XVIII) may be prepared from compounds of general formula (V) by reaction with a compound of general formula (XVII), wherein $R^d$ is O, as described for the preparation of compounds of general formula (XIX) from compounds of general formula (V).

Scheme 5

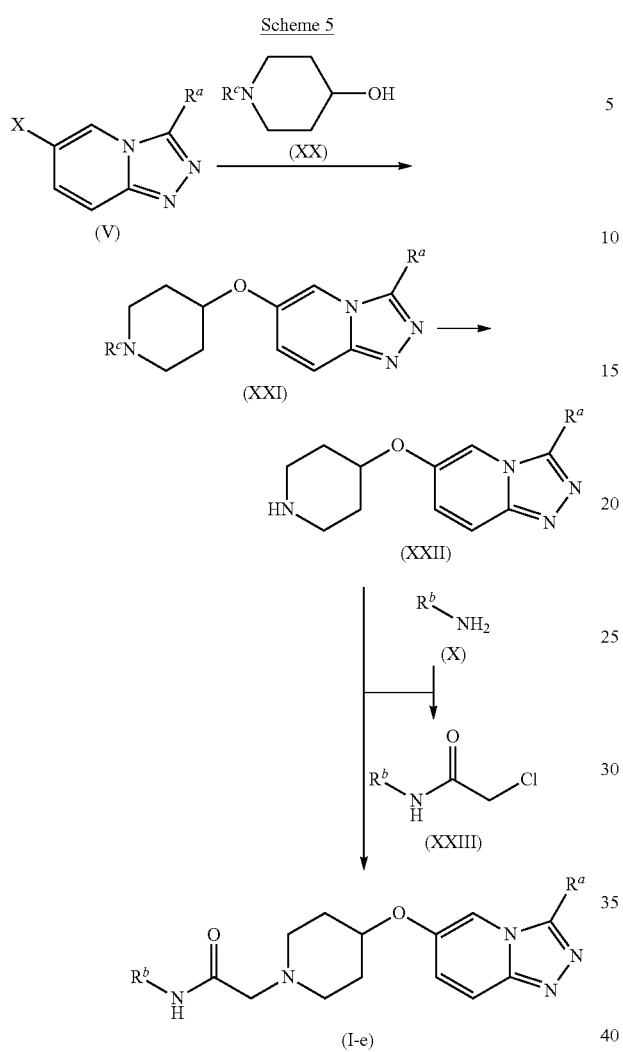

Compounds of general formula (I-e) may be prepared from compounds of general formula (XXII):

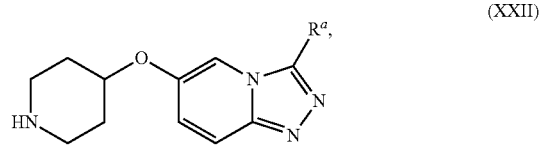

by reaction with a compound of general formula (XXIII):

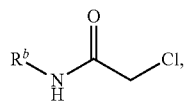

using a suitable base such as diisopropylethylamine, potassium carbonate, sodium carbonate or sodium hydride in the absence or presence of a suitable catalyst such as potassium iodide or sodium iodide, in a suitable solvent such as dichloromethane, tetrahydrofuran or acetonitrile, at a range of temperatures, preferably between room temperature and 80° C.

Compounds of general formula (XXIII) may be prepared from amines of general formula (X), according to known literature procedures (e.g. Migliara et al. *Farmaco* (1992), 47(1), 111-19).

Compounds of general formula (XXII) may be prepared from compounds of general formula (XXI):

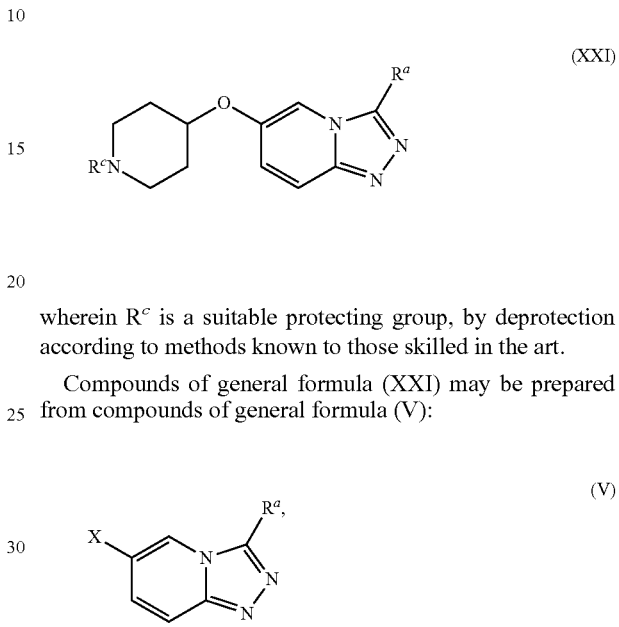

wherein $R^c$ is a suitable protecting group, by deprotection according to methods known to those skilled in the art.

Compounds of general formula (XXI) may be prepared from compounds of general formula (V):

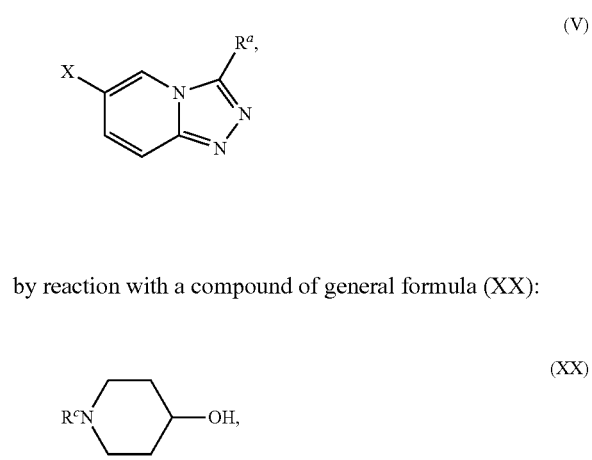

by reaction with a compound of general formula (XX):

as described for the preparation of compounds of formula (XII) from compounds of formula (XI).

Scheme 6

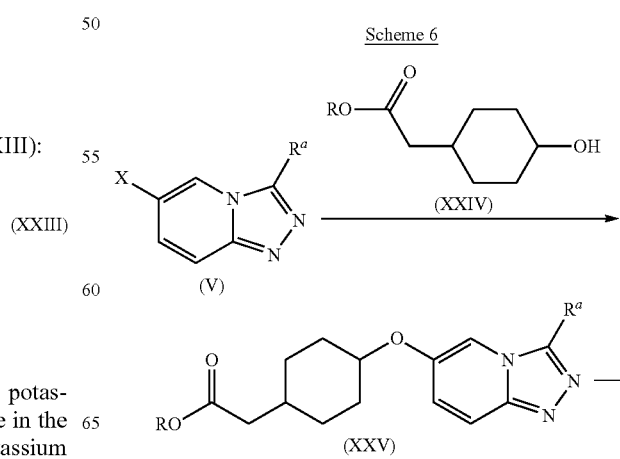

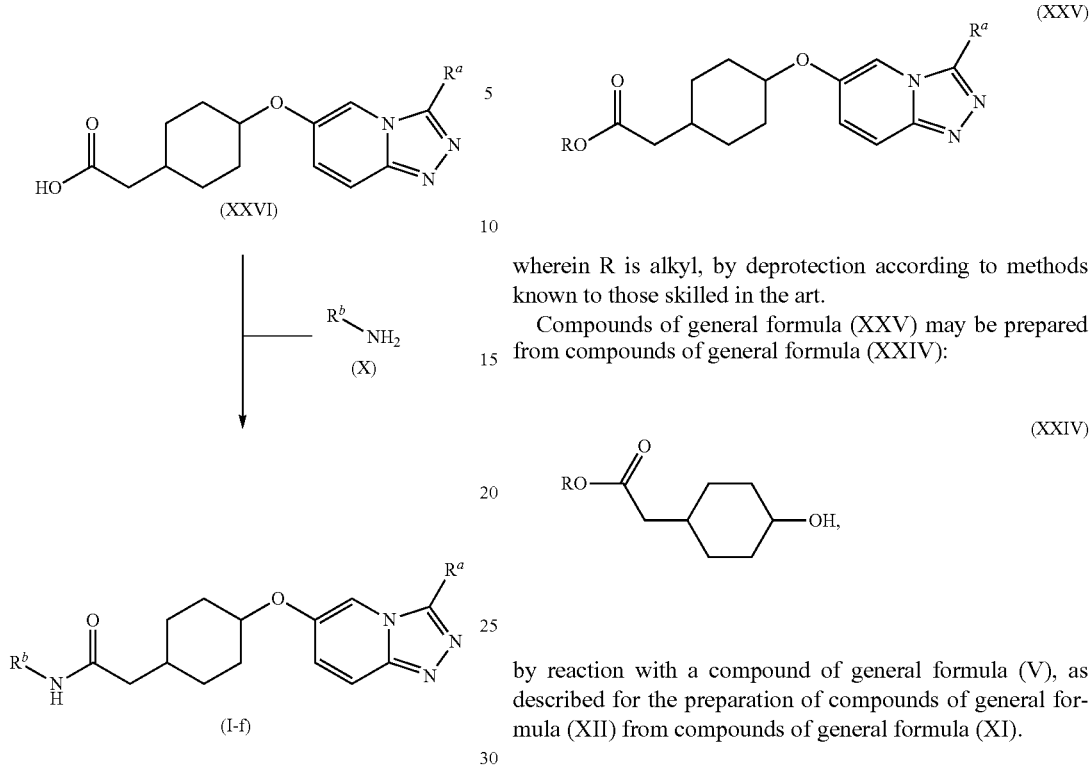

wherein R is alkyl, by deprotection according to methods known to those skilled in the art.

Compounds of general formula (XXV) may be prepared from compounds of general formula (XXIV):

by reaction with a compound of general formula (V), as described for the preparation of compounds of general formula (XII) from compounds of general formula (XI).

Compounds of general formula (I-f) may be prepared from compounds of general formula (XXVI):

by reaction with amines of formula (X) as described for the preparation of compounds of general formula (I-a) from compounds of general formula (IX).

Compounds of general formula (XXVI) may be prepared from compounds of general formula (XXV):

Scheme 7

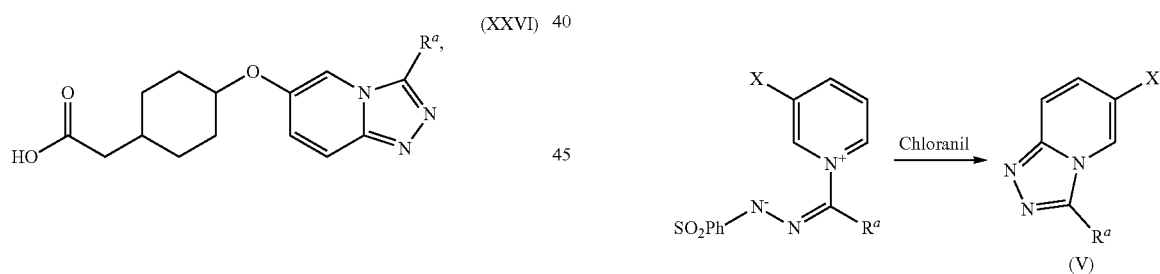

Compounds of general formula (V) may be prepared as described in *Chem. Soc. Jpn.*, 1980, 53, 2007-11.

Scheme 8

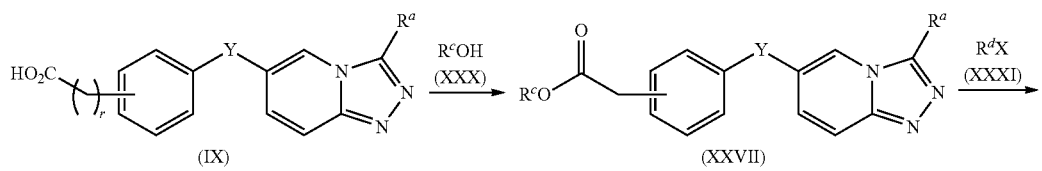

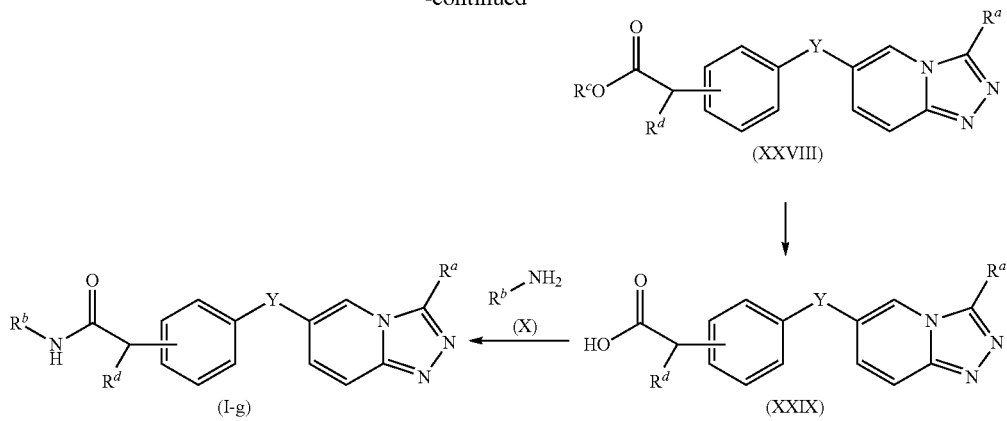

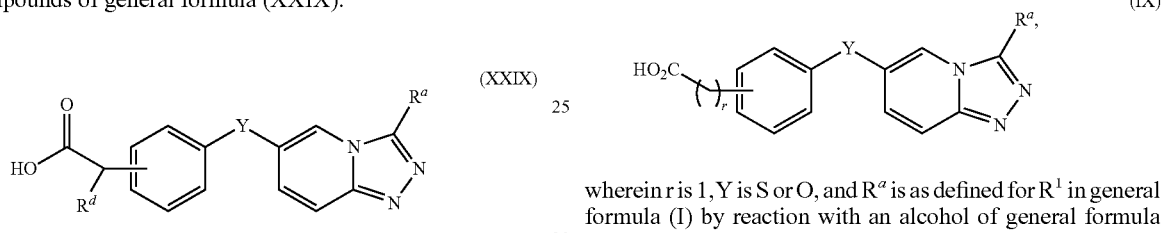

Compounds of general formula (I-g) may be prepared from compounds of general formula (XXIX):

by reaction with an amine of general formula (X):

R$^b$NH$_2$ (X), wherein R$^b$ is as defined for R$^2$ in general formula (I) as described above.

Compounds of general formula (XXIX) may be prepared from compounds of general formula (XXVIII):

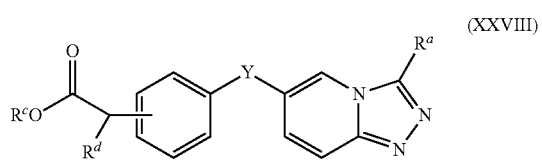

wherein R$^c$ is alkyl by deprotection according to methods known to those skilled in the art.

Compounds of general formula (XXVIII) may be prepared from compounds of general formula (XXVII):

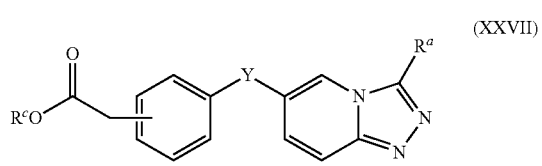

by reaction with a suitable compound R$^d$X (XXXI) using a suitable base such as lithium hexamethyldisilazide or sodium hydride in a suitable solvent such as tetrahydrofuran, DMF or diethyl ether, at a range of temperatures, preferably between room temperature and 80° C.

Compounds of general formula (XXVII) may be prepared from compounds of general formula (IX):

wherein r is 1, Y is S or O, and R$^a$ is as defined for R$^1$ in general formula (I) by reaction with an alcohol of general formula (XXX) according to methods known to those skilled in the art.

R$^c$OH  (XXX)

General Experimental Details

Abbreviations used in the experimental section:
aq.=aqueous;
DCM=dichloromethane;
DIPEA=diisopropylethylamine;
DMF=N,N-dimethylformamide;
DMSO=dimethyl sulfoxide;
EDCl HCl=1-ethyl-3-(3'-dimethylaminopropyl)carbodiimide hydrochloride;
EtOAc=ethyl acetate;
EtOH=ethanol;
FCC=flash column chromatography;
h=hour;
HATU=2-(7-aza-1H-benzotriazole-1-yl)-1,1,3,3-tetramethyluronium hexafluorophosphate;
HOBt=1-hydroxy-benzotriazole;
HPLC=high performance liquid chromatography;
LCMS=liquid chromatography mass spectrometry;
MeCN=acetonitrile;
MeOH=methanol;
min=minutes;
NMR=nuclear magnetic resonance;
RT=room temperature;
Rt=retention time;
sat.=saturated;
SCX-2=strong cation exchange chromatography;
TFA=trifluoroacetic acid; THF=tetrahydrofuran.

The nomenclature of structures was assigned using Autonom 2000 Name software from MDL Inc.

All reactions were carried out under an atmosphere of nitrogen unless specified otherwise.

NMR spectra were obtained on a Varian Unity (nova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane. NMR spectra were assigned using Data-Chord Spectrum Analyst Version 4.0.b21.

Where products were purified by flash column chromatography, 'flash silica' refers to silica gel for chromatography, 0.035 to 0.070 mm (220 to 440 mesh) (e.g. Fluka silica gel 60), and an applied pressure of nitrogen up to 10 p.s.i accelerated column elution or use of the CombiFlash® Companion purification system or use of the Biotage SP1 purification system. All solvents and commercial reagents were used as received.

Compounds purified by preparative HPLC were purified using a C18-reverse-phase column (100×22.5 mm i.d Genesis column with 7 μm particle size), or a Phenyl-Hexyl column (250×21.2 mm i.d. Gemini column with 5 μm particle size), UV detection at 230 or 254 nm, flow 5-20 mL/min), eluting with gradients from 100-0 to 0-100% water/acetonitrile (containing 0.1% TFA or 0.1% formic acid) or water/MeOH (containing 0.1% TFA or 0.1% formic acid). Fractions containing the required product (identified by LCMS analysis) were pooled, the organic fraction removed by evaporation, and the remaining aqueous fraction lyophilised, to give the final product. Products purified by preparative HPLC were isolated as formate or TFA salts, unless otherwise stated.

The Liquid Chromatography Mass Spectroscopy (LCMS) and HPLC systems used are:

Method 1

Waters ZMD quadrupole mass spectrometer with a C18-reverse-phase column (30×4.6 mm Phenomenex Luna 3 μm particle size), elution with A: water+0.1% formic acid; B: acetonitrile+0.1% formic acid. Gradient:

| Gradient - Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 μL split to MS with in-line UV detector). MS ionization method—Electrospray (positive and negative ion).

Method 2

Waters Platform LC Quadrupole mass spectrometer with a C18-reverse-phase column (30×4.6 mm Phenomenex Luna 3 μm particle size), elution with A: water+0.1% formic acid; B: acetonitrile+0.1% formic acid. Gradient:

| Gradient - Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 μL split to MS with in-line UV detector). MS ionization method—Electrospray (positive and negative ion).

Method 3

Phenomenex Gemini C18-reverse-phase column (250×21.20 mm 5 μm particle size), elution with A: water+0.1% formic acid; B: acetonitrile+0.1% formic acid. Gradient −95% A/5% B to 5% A/95% B over 15 min—flow rate 18 mL/min. Detection—In-line UV detector set at 220 nM wavelength.

Method 4

Waters Micromass ZQ2000 with a C18-reverse-phase column (100×3.0 mm Higgins Clipeus with 5 μm particle size), elution with A: water+0.1% formic acid; B: acetonitrile+0.1% formic acid. Gradient:

| Gradient - Time | flow mL/min | % A | % B |
| --- | --- | --- | --- |
| 0.00 | 1.0 | 95 | 5 |
| 1.00 | 1.0 | 95 | 5 |
| 15.00 | 1.0 | 5 | 95 |
| 20.00 | 1.0 | 5 | 95 |
| 22.00 | 1.0 | 95 | 5 |
| 25.00 | 1.0 | 95 | 5 |

Detection—MS, ELS, UV (100 μL split to MS with in-line UV detector). MS ionisation method—Electrospray (positive ion).

Method 5

Waters Platform LC Quadrupole mass spectrometer with a C18-reverse-phase column (30×4.6 mm Phenomenex Luna 3 μm particle size), elution with A: water+0.1% formic acid; B: methanol+0.1% formic acid. Gradient:

| Gradient - Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 μL split to MS with in-line HP1100 DAD detector). MS ionization method—Electrospray (positive and negative ion).

Method 6

Phenomenex Gemini C18-reverse-phase column (250×21.20 mm 5 μm particle size), elution with A: water+0.1% formic acid; B: methanol+0.1% formic acid. Gradient −95% A/5% B to 5% A/95% B over 15 min—flow rate 18 mL/min. Detection—In-line UV detector set at 254 nM wavelength.

Method 7

Waters Micromass ZQ2000 with a C18-reverse-phase column (100×3.0 mm Higgins Clipeus with 5 μm particle size), elution with A: water+0.1% formic acid; B: methanol+0.1% formic acid. Gradient:

| Gradient - Time | flow mL/min | % A | % B |
| --- | --- | --- | --- |
| 0.00 | 1.0 | 85 | 15 |
| 1.00 | 1.0 | 85 | 15 |
| 13.00 | 1.0 | 5 | 95 |
| 20.00 | 1.0 | 5 | 95 |
| 22.00 | 1.0 | 85 | 15 |
| 25.00 | 1.0 | 85 | 15 |

Detection—MS, ELS, UV (100 μL split to MS with in-line UV detector). MS ionisation method—Electrospray (positive ion).

Method 8

Waters ZMD quadrupole mass spectrometer with a C18-reverse-phase column (30×4.6 mm Phenomenex Luna 3 μm particle size), elution with A: water+0.1% formic acid; B: methanol+0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 μL split to MS with in-line Waters 996 DAD detector). MS ionization method—Electrospray (positive and negative ion).

Method 9

Waters Micromass ZQ2000 with a Acquity BEH C18 column (50×2.1 mm with 1.7 μm particle size), elution with A: water+0.1% formic acid; B: methanol+0.1% formic acid. Gradient:

| Gradient - Time | flow mL/min | % A | % B |
|---|---|---|---|
| 0.00 | 0.4 | 85 | 15 |
| 0.40 | 0.4 | 85 | 15 |
| 6.00 | 0.4 | 5 | 95 |
| 8.00 | 0.4 | 5 | 95 |
| 8.80 | 0.4 | 85 | 15 |
| 10.00 | 0.4 | 85 | 15 |

Detection—MS, UV PDA. MS ionisation method—Electrospray (positive/negative ion).

Method 10

Waters Quatro Microtriple quadrupole with a C18-reverse-phase column (100×3.0 mm Higgins Clipeus with 5 μm particle size), elution with A: water+0.1% formic acid; B: methanol+0.1% formic acid. Gradient:

| Gradient - Time | flow mL/min | % A | % B |
|---|---|---|---|
| 0.00 | 1.0 | 85 | 15 |
| 1.00 | 1.0 | 85 | 15 |
| 13.00 | 1.0 | 5 | 95 |
| 20.00 | 1.0 | 5 | 95 |
| 22.00 | 1.0 | 85 | 15 |
| 25.00 | 1.0 | 85 | 15 |

Detection—MS, ELS, UV (100 μL split to MS with in-line UV detector). MS ionisation method—Electrospray (positive/negative ion).

Method 11

Waters ZMD quadrupole mass spectrometer with a C18-reverse-phase column (Acquity BEH C18 reverse column, 1.7 um, 100×2.1 mm), elution with A: water+0.1% formic acid; B: acetonitrile+0.1% formic acid. Gradient:

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionisation method—Electrospray (positive/negative ion).

EXAMPLE 1

N-Cyclopropylmethyl-3-{3-[3-(2-morpholin-4-yl-ethoxy)-phenyl]-[1,2,4]triazolo[4,3-a]pyridin-6-yl-sulfanyl}-benzamide

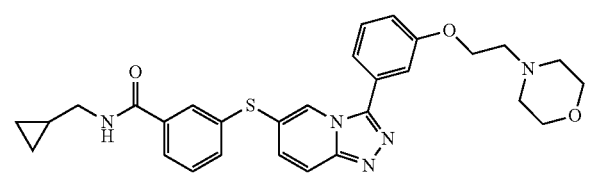 [SMILES: O=C(NCC1CC1)c1cccc(Sc2ccc3nnc(-c4cccc(OCCN5CCOCC5)c4)n3c2)c1]

a. N-(5-Iodo-pyridin-2-yl)-N'-[1-[3-(2-morpholin-4-yl-ethoxy)-phenyl]-meth-(E)-ylidene]-hydrazine

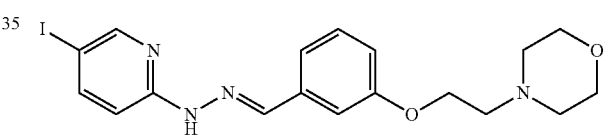

To a suspension of 5-iodo-2-hydrazinopyridine (6.62 g, 0.028 mmol) in EtOH (90 mL) was added 3-(2-morpholin-4-yl-ethoxy)-benzaldehyde (6.63 g, 0.028 mmol). The reaction was heated at reflux for 2 h under nitrogen, then cooled to RT. The resulting precipitate was collected by filtration and washed with EtOH to afford the title compound (10.93 g, 86%) as a white solid. LCMS (Method 1): Rt 2.37 min, m/z 453 [MH$^+$]. $^1$H NMR (300 MHz, CD$_3$OD): δ 8.24 (1 H, d, J 2.2), 7.90-7.84 (2 H, m), 7.36-7.18 (3 H, m), 7.12 (1 H, d, J 8.8), 6.94-6.89 (1 H, m), 4.19 (2 H, t, J 5.4), 3.72 (4 H, t, J 4.6), 2.83 (2 H, t, J 5.4), 2.62 (4 H, t, J 4.6).

b. 6-Iodo-3-[3-(2-morpholin-4-yl-ethoxy)-phenyl]-[1,2,4]triazolo[4,3-a]pyridine

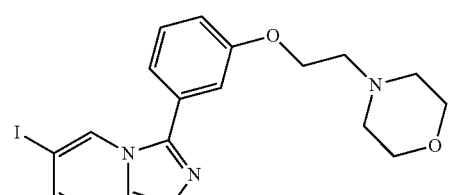

To a solution of Example 1 step a (10.93 g, 24.16 mmol) in DCM (100 mL)/EtOH (15 mL), was added PhI(OAc)₂ (10.74 g, 33.35 mmol). The reaction was stirred at RT for 72 h, diluted with DCM (25 mL) then washed with aq. sodium hydroxide (1 M, 25 mL) and brine (25 mL). The organic layer was dried (MgSO₄), filtered, and the filtrate was concentrated in vacuo. The residue was triturated with Et₂O (10 mL) and the resulting solid was collected by filtration to afford the title compound (9.98 g, 92%) as an off-white solid. LCMS (Method 1): Rt 2.11 min, m/z 451 [MH⁺]. ¹H NMR (400 MHz, DMSO-d₆): δ 8.69 (1 H, s), 7.71 (1 H, d, J 9.5), 7.60 (1 H, d, J 9.5), 7.53 (1 H, t, J 7.9), 7.47-7.41 (2 H, m), 7.18 (1 H, d, J 8.1), 4.21 (2 H, t, J 5.7), 3.59 (4 H, t, J 4.5), 2.75 (2 H, t, J 5.7), 2.45 (4 H, m).

c. 3-{3-[3-(2-Morpholin-4-yl-ethoxy)-phenyl]-[1,2,4]-triazolo[4,3-a]pyridin-6-ylsulfanyl}-benzoic acid

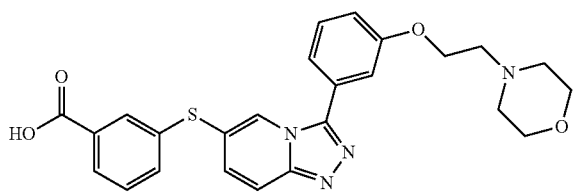 [SMILES: O=C(O)c1cccc(Sc2ccc3nnc(-c4cccc(OCCN5CCOCC5)c4)n3c2)c1]

A reaction vessel was charged with Example 1 step b (400 mg, 0.888 mmol), 3-mercaptobenzoic acid (205 mg, 1.24 mmol), [1,1'-bis(diphenylphosphino)ferrocene]dichloropalladium(II) 1:1 complex with DCM (138 mg, 0.168 mmol), cesium carbonate (578 mg, 1.777 mmol), and DMF (3 mL). The reaction was degassed (×3) under argon. The reaction was heated at 90° C. for 24 h then allowed to cool to RT, filtered, and the filtrate concentrated in vacuo to afford the title compound (422 mg, quantitative). LCMS (Method 2): Rt 2.20 min, m/z 477 [MH⁺].

d. N-Cyclopropylmethyl-3-{3-[3-(2-morpholin-4-yl-ethoxy)-phenyl]-[1,2,4]triazolo[4,3-a]pyridin-6-yl-sulfanyl}-benzamide A reaction vessel was charged with Example 1 step c (213 mg, 0.447 mmol), cyclopropanemethylamine (32 mg, 0.447 mmol), HATU (212 mg, 0.558 mmol), and DMF (3 mL). DIPEA (225 µL, 1.34 mmol) was added, the reaction was stirred at RT for 24 h then concentrated in vacuo and the crude residue purified directly by reverse phase preparative HPLC (Method 3) to afford the title compound (92 mg, 39%) as an off-white solid. LCMS (Method 4): Rt 6.55 min, m/z 530 [MH⁺]. ¹H NMR (400 MHz, CDCl₃): δ 8.39 (1 H, s), 7.89 (1 H, s), 7.75-7.65 (2 H, m), 7.51-7.30 (5 H, m), 7.17 (1 H, d, J 9.6), 7.08 (1 H, d, J 8.4), 6.85 (1 H, m), 4.25 (2 H, t, J 5.2), 3.79 (4 H, t, J 4.4), 3.26 (2 H, t, J 6.2), 3.00 (2 H, t, J 5.2), 2.77 (4 H, m), 1.07-0.95 (1 H, m), 0.52-0.44 (2 H, m), 0.24-0.18 (2 H, m).

The following Examples were prepared using similar methods to that used in Example 1.

| Example No. | Structure | NMR (400 MHz) δ | LCMS |
|---|---|---|---|
| 2 | 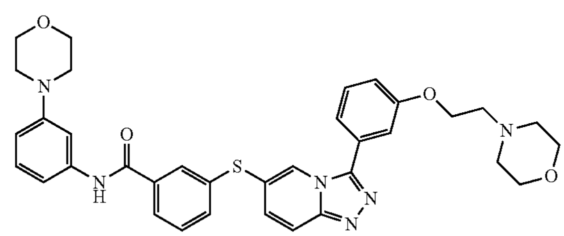 [SMILES: O=C(Nc1cccc(N2CCOCC2)c1)c1cccc(Sc2ccc3nnc(-c4cccc(OCCN5CCOCC5)c4)n3c2)c1] | (CDCl₃): 8.63 (1H, s), 8.35 (1H, s), 8.00 (1H, s), 7.82 (1H, d, J 7.5), 7.54 (1H, d, J 9.5), 7.50-7.40 (4H, m), 7.34-7.28 (2H, m), 7.18 (1H, t, J 8.1), 7.14-7.03 (2H, m), 6.99 (1H, d, J 8), 6.66 (1H, dd, J 8.3, 2.4), 4.16 (2H, t, J 5.6), 3.79 (4H, t, J 4.6), 3.73 (4H, t, J 4.6), 3.11 (4H, t, J 4.7), 2.85 (2H, t, J 5.5), 2.60 (4H, t, J 4.4). | (Method 3): Rt 7.15 min, m/z 637 [MH⁺]. |
| 3 | 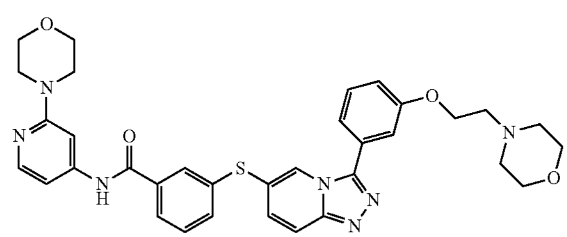 [SMILES: O=C(Nc1ccnc(N2CCOCC2)c1)c1cccc(Sc2ccc3nnc(-c4cccc(OCCN5CCOCC5)c4)n3c2)c1] | (CDCl₃): 8.80 (1H, br s), 8.39 (1H, t, J 1.2), 8.07 (1H, d, J 5.7), 7.97 (1H, t, J 1.7), 7.81 (1H, dt, J 7.6, 1.5), 7.59 (1H, dd, J 9.5, 1), 7.55-7.44 (3H, m), 7.40-7.32 (3H, m), 7.16 (1H, dd, J 1.6, 0.3), 7.10 (1H, dd, J 2.6, 1), 6.75 (1H, dd, J 5.7, 1.7), 4.24 (2H, t, J 5.3), 3.78 (8H, m), 3.49 (4H, t, J 4.8), 2.97 (2H, t, J 5.3), 2.75 (4H, t, J 4.5) | (Method 4): Rt 5.49 min, m/z 638 [MH⁺]. |
| 4 | 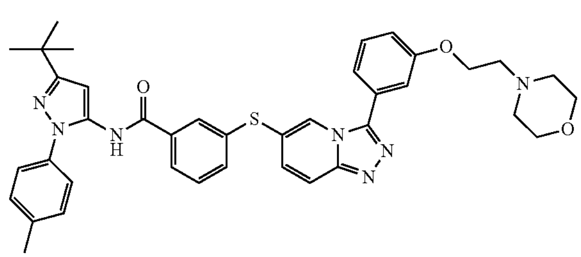 | (CDCl₃): 8.41 (1H, s), 7.75 (1H, d, J 9.6), 7.49 (1H, t, J 8), 7.40 (1H, s), 7.35 (1H, d, J 7.7), 7.26 (2H, d, J 5.5), 7.19-7.10 (5H, m), 7.13-7.05 (4H, m), 6.59 (1H, s), 4.25 (2H, t, J 5.5), 3.79 (4H, t, J 4.5), 3.65 (2H, s), 2.93 (2H, t, J 5.5), 2.70 (4H, t, J 4.3), 2.37 (3H, s), 1.32 (9H, s). | (Method 4): Rt 8.32 min, m/z 702 [MH⁺]. |

-continued

| Example No. | Structure | NMR (400 MHz) δ | LCMS |
|---|---|---|---|
| 5 | 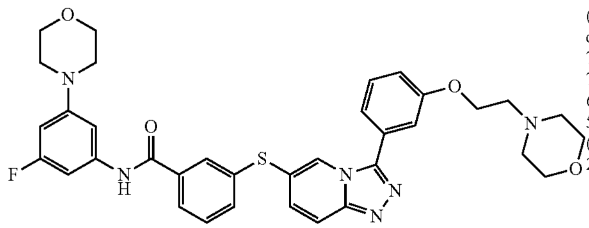 [SMILES: O=C(Nc1cc(F)cc(N2CCOCC2)c1)c1cccc(Sc2ccc3nnc(-c4cccc(OCCN5CCOCC5)c4)n3c2)c1] | (CDCl₃): 8.39 (1H, s), 7.69 (1H, d, J 9.5), 7.47 (1H, t, J 8), 7.37-7.25 (7H, m), 7.17 (1H, d, J 9.7), 7.07 (2H, m), 6.69 (1H, d, J 10), 6.29 (1H, d, 11.8), 4.18 (2H, t, J 5.2), 3.79-3.71 (8H, m), 3.69 (2H, s), 3.08 (4H, t, J 4.5), 2.85 (2H, t, J 5.5), 2.61 (4H, m). | (Method 3): Rt 7.59 min, m/z 669 [MH⁺]. |
| 6 | 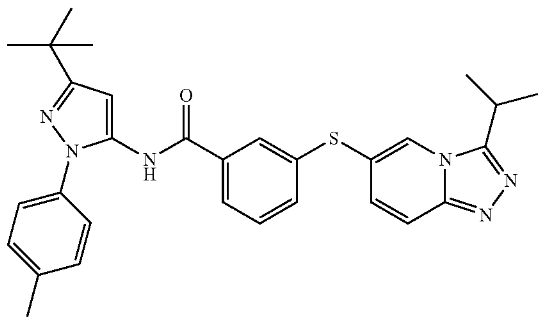 | (CD₃OD): 8.50 (1H, s), 7.64 (1H, d, J 9.6), 7.32 (2H, d, J 8.1), 7.28 (1H, dd, J 9.6, 1.6), 7.21-7.15 (6H, m), 6.30 (1H, s), 3.57 (2H, s), 3.53 (1H, m), 2.32 (3H, s), 1.47 (3H, s), 1.45 (3H, s), 1.30 (9H, s). | (Method 4): Rt 11.35 min, m/z 539 [MH⁺]. |
| 7 | 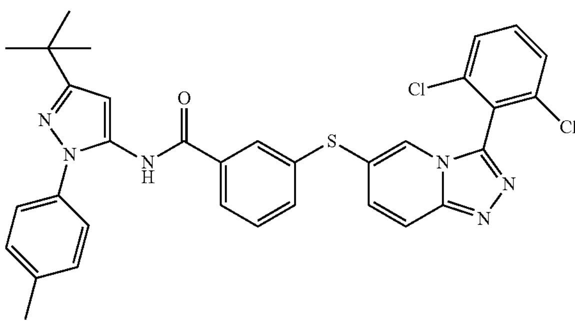 | (CD₃OD): 7.89 (1H, s), 7.84 (1H, dd, J 9.6, 1.0), 7.64-7.53 (3H, m), 7.43 (1H, dd, J 9.6, 1.6), 7.35-7.28 (2H, m), 7.22-7.15 (2H, m), 7.15 (4H, s), 6.32 (1H, s), 3.57 (2H, s), 2.31 (3H, s), 1.31 (9H, s). | (Method 4): Rt 12.70 min, m/z 641 [MH⁺]. |
| 8 | 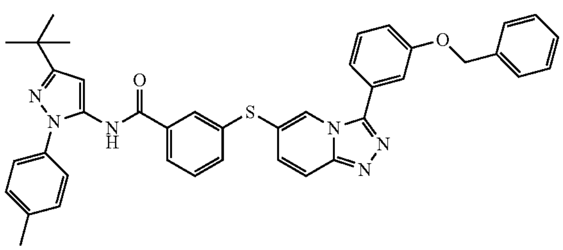 | (CD₃OD): 8.26 (1H, t, J 1.2), 7.75-7.68 (1H, m), 7.48 (1H, t, J 8.0), 7.44 (2H, d, J 7.5), 7.40 (1H, t, J 2.0), 7.38-7.25 (7H, m), 7.22-7.08 (7H, m), 6.32 (1H, s), 5.13 (2H, s), 3.53 (2H, s), 2.29 (3H, s), 1.38-1.20 (9H, m). | (Method 7): Rt 13.44 min, m/z 679 [MH⁺]. |
| 9 | 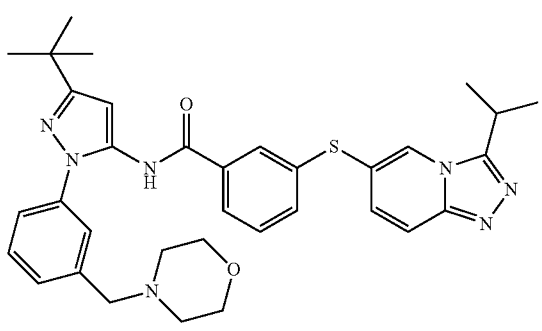 | (CDCl₃): 8.07 (1H, s), 7.68 (1H, d, J 9.6), 7.33 (3H, m), 7.29-7.13 (5H, m), 7.07 (2H, dd, J 9.5, 1.7), 6.59 (1H, s), 3.80-3.59 (6H, m), 3.52 (2H, m), 3.41-3.30 (1H, m), 2.47 (4H, m), 1.55 (3H, s), 1.53 (3H, s), 1.32 (9H, s). | (Method 9): Rt 4.11 min, m/z 624 [MH⁺]. |

EXAMPLE 10

1-(5-tert-Butyl-2-p-tolyl-2H-pyrazol-3-yl)-3-(4-{3-[3-(2-morpholin-4-yl-ethoxy)-phenyl]-[1,2,4]triazolo[4,3-a]pyridin-6-ylsulfanyl}-phenyl)-urea

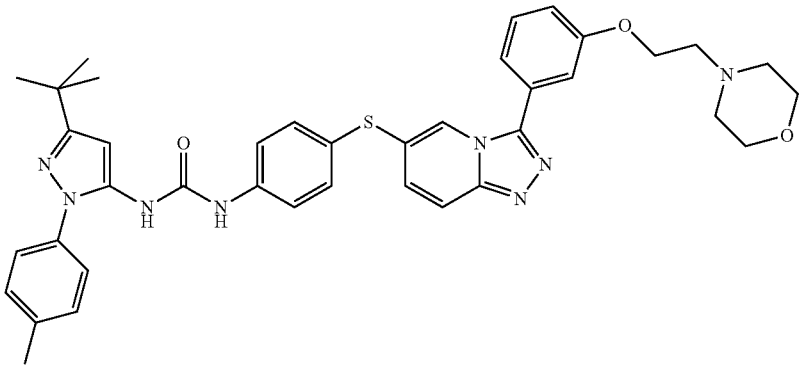 [SMILES: Cc1ccc(-n2nc(C(C)(C)C)cc2NC(=O)Nc2ccc(Sc3ccc4nnc(-c5cccc(OCCN6CCOCC6)c5)n4c3)cc2)cc1]

a. 3-(6-Bromo-[1,2,4]triazolo[4,3-a]pyridin-3-yl)-phenol

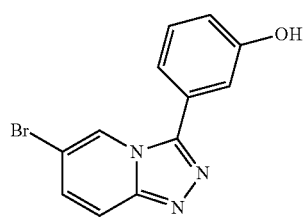 [SMILES: Oc1cccc(-c2nnc3ccc(Br)cn23)c1]

Boron tribromide (1 M in DCM, 13.1 mL, 13.1 mmol) was added slowly to a stirred solution of 3-(3-benzyloxy-phenyl)-6-bromo-[1,2,4]triazolo[4,3-a]pyridine (1 g, 2.63 mmol) in DCM (5 mL) at −78° C. The reaction was allowed to warm up to RT, stirred for 24 h, and treated with sat. NaHCO$_3$ solution until pH>7. The product was extracted with DCM:MeOH 9:1 (mL), dried (MgSO$_4$), and concentrated in vacuo. Purification of the crude residue by FCC (DCM:MeOH, 1:0 to 9:1) afforded the title compound (350 mg, 46%) as a yellow solid. LCMS (Method 2): Rt 2.65 min, m/z 290 and 292 [MH$^+$].

b. 6-Bromo-3-[3-(2-morpholin-4-yl-ethoxy)-phenyl]-[1,2,4]-triazolo[4,3-a]pyridine

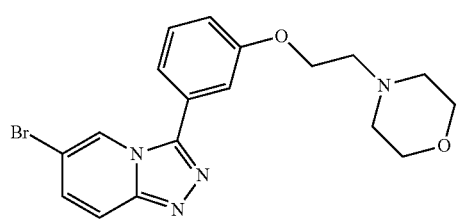 [SMILES: Brc1ccc2nnc(-c3cccc(OCCN4CCOCC4)c3)n2c1]

A mixture of Example 10 step a (250 mg, 1.21 mmol), N-(2-bromoethyl)morpholine hydrochloride (306 mg, 1.32 mmol) and K$_2$CO$_3$ (500 mg, 3.62 mmol) in DMF (20 mL) was heated at 50° C. for 24 h. The reaction was then allowed to cool to RT and concentrated in vacuo. The residue was purified by FCC (DCM:MeOH, 1:0 to 9:1) to afford the title compound (479 mg, 98%) as a yellow oil. $^1$H NMR (300 MHz, CDCl$_3$): δ 8.44 (1 H, dd, J 1.7, 1), 7.74-7.69 (1 H, m), 7.50 (1 H, t, J 7.9), 7.39-7.35 (2 H, m), 7.35-7.30 (1 H, m), 7.14-7.08 (1 H, m), 4.21 (2 H, t, J 5.6), 3.74 (4 H, t, J 4.6), 2.85 (2 H, t, J 5.6), 2.63-2.56 (4 H, m).

c. 4-{3-[3-(2-Morpholin-4-yl-ethoxy)-phenyl]-[1,2,4]triazolo[4,3-a]pyridin-6-ylsulfanyl}-phenylamine

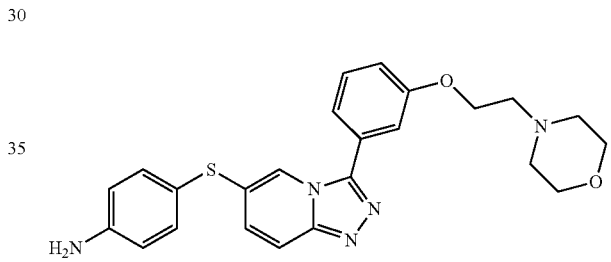

The title compound was prepared in a similar manner to Example 1 step c using Example 10 step b and 4-amino-benzene-thiol. LCMS (Method 2): Rt 2.14 min, m/z 448 [MH$^+$].

d. 1-(5-tert-Butyl-2-p-tolyl-2H-pyrazol-3-yl)-3-(4-{3-[3-(2-morpholin-4-yl-ethoxy)-phenyl]-[1,2,4]triazolo[4,3-a]pyridin-6-ylsulfanyl}-phenyl)-urea A mixture of Example 10 step c (315 mg, 0.703 mmol), 5-(2,2,2-trichloroethoxycarbonyl)amino-3-tert-butyl-1-p-tolyl-1H-pyrazole (299 mg, 0.703 mmol) and DIPEA (116 μL, 0.675 mmol) in DMSO (3 mL) was heated at 55° C. for 24 h. The reaction was concentrated in vacuo and the residue purified by reverse phase preparative HPLC (Method 3) to afford the title compound (202 mg, 41%) as an off-white solid. LCMS (Method 4): Rt 8.46 min, m/z 703 [MH$^+$]. $^1$H NMR (400 MHz, CDCl$_3$): δ 9.30 (1 H, br s), 8.34 (1 H, br s), 8.16 (1 H, s), 7.49-7.41 (3 H, m), 7.37 (1 H, d, J 9.6), 7.29 (2 H, d, J 8.4), 7.25-7.20 (2 H, m), 7.18 (2 H, d, J 8), 7.09-7.04 (2 H, m), 6.90 (2 H, d, J 8), 6.44 (1 H, s), 4.15 (2 H, t, J 5.4), 3.72 (4 H, t, J 4.5), 2.88 (2 H, t, J 5.4), 2.64 (4 H, t, J 4.4), 2.11 (3 H, s), 1.30 (9 H, s).

The following Example was prepared using similar methods to those used in Example 10 (steps c-d):

| Example No. | Structure | NMR (400 MHz) δ | LCMS |
|---|---|---|---|
| 11 | 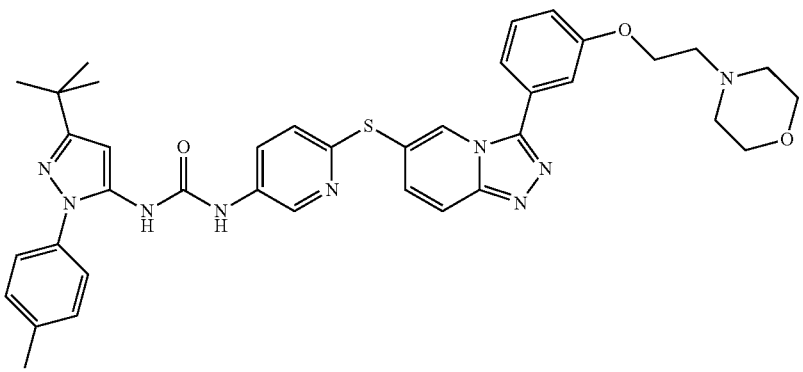 | (CDCl$_3$): 9.42 (1H, bs), 8.43 (1H, bs), 8.12 (1H, s), 7.48-7.29 (8H, m), 7.30-7.23 (4H, m), 7.21-7.09 (4H, m), 7.03 (1H, dd, J 9.6, 1.6), 6.81 (2H, d, J 8.1), 6.45 (1H, s), 5.06 (2H, s), 2.04 (3H, s), 1.29 (9H, s). | (Method 4): Rt 13.95 min, m/z 680 [MH$^+$]. |

EXAMPLE 12

1-(5-tert-Butyl-2-p-tolyl-2H-pyrazol-3-yl)-3-(6-{3-[3-(2-morpholin-4-yl-ethoxy)-phenyl]-[1,2,4]triazolo[4,3-a]pyridin-6-ylsulfanyl}-pyridin-3-yl)-urea

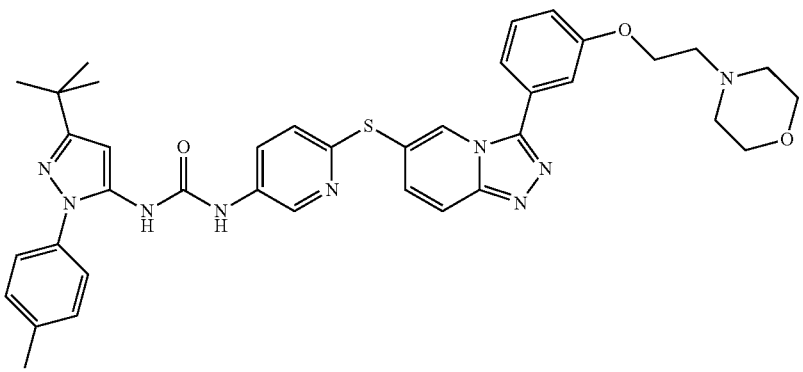 [SMILES: Cc1ccc(-n2nc(C(C)(C)C)cc2NC(=O)Nc2ccc(Sc3ccc4nnc(-c5cccc(OCCN6CCOCC6)c5)n4c3)nc2)cc1]

a. 3-[3-(2-Morpholin-4-yl-ethoxy)-phenyl]-6-(5-nitro-pyridin-2-ylsulfanyl)-[1,2,4]triazolo[4,3-a]pyridine

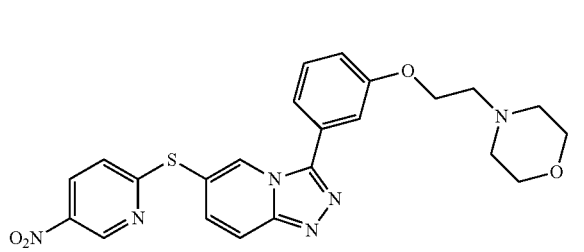 [SMILES: O=[N+]([O-])c1ccc(Sc2ccc3nnc(-c4cccc(OCCN5CCOCC5)c4)n3c2)nc1]

To a solution of Example 1 step b (300 mg, 0.67 mmol) in THF (5 mL) at 0° C. was added dropwise 2 M isopropylmagnesium chloride in Et$_2$O (335 µL, 0.67 mmol). The reaction was stirred at 0° C. for 1 h, then 2,2'-dithiobis(5-nitro-pyridine) (227 mg, 0.73 mmol) was added. The reaction was allowed to warm to RT and stirred for an additional 1 h then diluted with EtOAc (10 mL). The organic layer was washed with 1 M NaOH (10 mL), brine (10 mL), dried (MgSO$_4$), and concentrated in vacuo. Purification by reverse phase preparative HPLC (Method 3) afforded the title compound (50 mg, 16%) as a yellow solid. LCMS (Method 1): Rt 2.33 min, m/z 479 [MH$^+$]. $^1$H NMR (400 MHz, CD$_3$OD): δ 9.16 (1 H, d, J 2.6), 8.80 (1 H, t, J 1.2), 8.41 (1 H, dd, J 8.9, 2.7), 7.90 (1 H, dd, J 9.6, 1), 7.60-7.53 (2 H, m), 7.50-7.45 (3 H, m), 7.25-7.20 (1 H, m), 4.27 (2 H, t, J 5.4), 3.73 (4 H, t, J 4.7), 2.94 (2 H, t, J 5.4), 2.70 (4 H, t, J 4.5).

b. 6-{3-[3-(2-Morpholin-4-yl-ethoxy)-phenyl]-[1,2,4]triazolo[4,3-a]pyridin-6-ylsulfanyl}-pyridin-3-ylamine

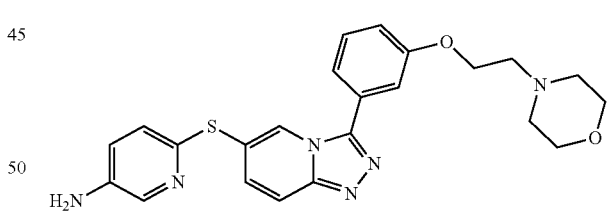

Example 12 step a (50 mg, 0.11 mmol) was dissolved in EtOH (10 mL) and treated with Pd/C (10%) (10 mg). The reaction was stirred at RT under an atmosphere of hydrogen over 72 h. The catalyst was filtered under nitrogen and the filtrate concentrated in vacuo to give the title compound (31 mg, 66%). LCMS (Method 1): Rt 1.94 min, m/z 449 [MH$^+$].

c. 1-(5-tert-Butyl-2-p-tolyl-2H-pyrazol-3-yl)-3-(6-{3-[3-(2-morpholin-4-yl-ethoxy)-phenyl]-[1,2,4]-triazolo[4,3-a]pyridin-6-ylsulfanyl}-pyridin-3-yl)-urea The title compound was prepared in a similar manner to Example 10 step d using Example 12 step b. LCMS (Method 4): Rt 8.06 min, m/z 704 [MH+]. ¹H NMR (400 MHz, CDCl₃): δ 8.70 (1 H, br s), 8.57 (1 H, s), 8.25 (1 H, dd, J 8.7, 2.7), 7.99 (1 H, d, J 2.7), 7.73 (1 H, br s), 7.63 (1 H, d, J 9.5), 7.47 (1 H, t, J 8), 7.35-7.23 (6 H, m), 7.09 (1 H, dd, J 8.4, 2.5), 7.04 (2 H, d, J 8), 6.45 (1 H, s), 4.20 (2 H, t, J 5.4), 3.73 (4 H, t, J 4.6), 2.91 (2 H, t, J 5.4), 2.67 (4 H, s), 2.22 (3 H, s), 1.34 (9 H, s).

EXAMPLE 13

1-(5-tert-Butyl-2-p-tolyl-2H-pyrazol-3-yl)-3-(5-{3-[3-(2-morpholin-4-yl-ethoxy)-phenyl]-[1,2,4]triazolo[4,3-a]pyridin-6-ylsulfanyl}-pyridin-2-yl)-urea

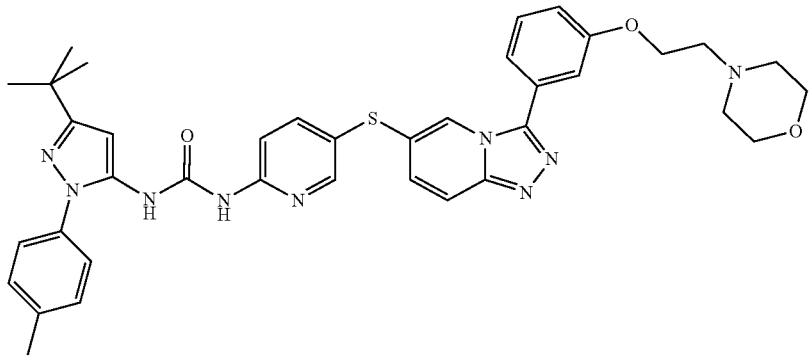 [SMILES: Cc1ccc(-n2nc(C(C)(C)C)cc2NC(=O)Nc2ccc(Sc3ccc4nnc(-c5cccc(OCCN6CCOCC6)c5)n4c3)cn2)cc1]

a. 5-{3-[3-(2-Morpholin-4-yl-ethoxy)-phenyl]-[1,2,4]triazolo[4,3-a]pyridin-6-ylsulfanyl}-pyridin-2-ylamine

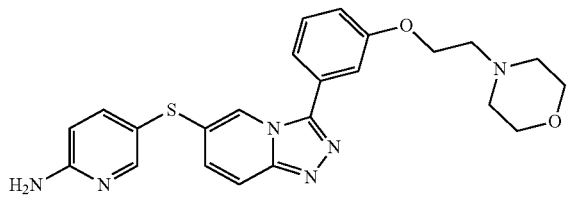 [SMILES: Nc1ccc(Sc2ccc3nnc(-c4cccc(OCCN5CCOCC5)c4)n3c2)cn1]

The title compound was prepared in a similar manner to Example 1 step c using 2-amino-5-mercaptopyridine dihydrochloride. LCMS (Method 1): Rt 1.77 min, m/z 449 [MH+].

b. 1-(5-tert-Butyl-2-p-tolyl-2H-pyrazol-3-yl)-3-(5-{3-[3-(2-morpholin-4-yl-ethoxy)-phenyl]-[1,2,4]triazolo[4,3-a]pyridin-6-ylsulfanyl}-pyridin-2-yl)-urea The title compound was prepared in a similar manner to Example 10 step d using Example 13 step a. LCMS (Method 4): Rt 8.25 min, m/z 704 [MH+]. ¹H NMR (400 MHz, CD₃OD): δ 8.31 (1 H, s), 7.84 (1 H, dd, J 8.7, 2.4), 7.81-7.77 (1 H, m), 7.74 (1 H, d, J 2.4), 7.55 (1 H, t, J 7.9), 7.41-7.33 (5 H, m), 7.30 (2 H, d, J 8.1), 7.22 (1 H, dd, J 8.4, 2.4), 7.03 (1 H, d, J 8.6), 6.51 (1 H, s), 4.26 (2 H, t, J 5.4), 3.75 (4 H, t, J 4.6), 2.97 (2 H, t, J 5.4), 2.74 (4 H, t, J 4.6), 2.26 (3 H, s), 1.34 (9 H, s).

EXAMPLE 14

1-(5-tert-Butyl-2-p-tolyl-2H-pyrazol-3-yl)-3-(trans-4-{3-[3-(2-morpholin-4-yl-ethoxy)-phenyl]-[1,2,4]triazolo[4,3-a]pyridin-6-yloxy}-cyclohexyl)-urea

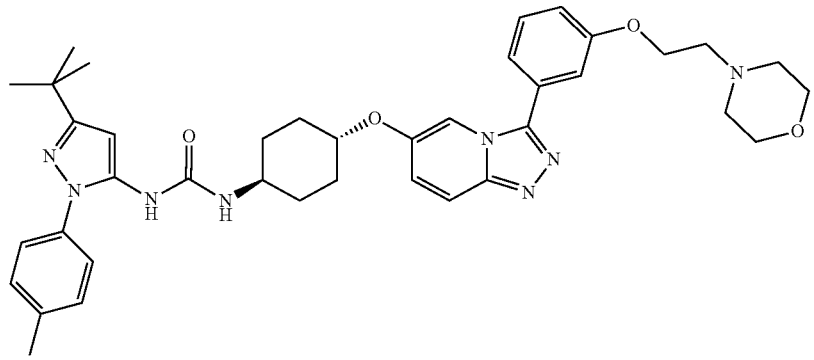 [SMILES: Cc1ccc(-n2nc(C(C)(C)C)cc2NC(=O)N[C@H]2CC[C@H](Oc3ccc4nnc(-c5cccc(OCCN6CCOCC6)c5)n4c3)CC2)cc1]

a. (trans-4-{3-[3-(2-Morpholin-4-yl-ethoxy)-phenyl]-[1,2,4]triazolo[4,3-a]pyridin-6-yloxy}-cyclohexyl)-carbamic acid tert-butyl ester

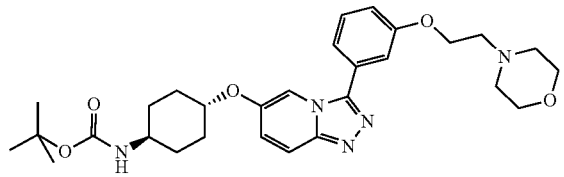 [SMILES: CC(C)(C)OC(=O)N[C@H]1CC[C@H](Oc2ccc3nnc(-c4cccc(OCCN5CCOCC5)c4)n3c2)CC1]

A mixture of Example 1 step b (234 mg, 0.52 mmol), copper (I) iodide (9 mg, 0.052 mmol), 1,10-phenanthroline (19 mg, 0.104 mmol), cesium carbonate (335 mg, 1.04 mmol) and trans-4-boc-aminocyclohexanol (560 mg, 2.6 mmol) in toluene (3 mL) was heated at 110° C. for 72 h under an argon atmosphere. The suspension was cooled to RT, diluted with EtOAc (10 mL) and filtered through HiFlo. The filtrate was concentrated in vacuo and the residue purified by reverse phase preparative HPLC (Method 3) to afford the title compound (205 mg, 39%) as an off-white solid. LCMS (Method 2): Rt 2.53 min, m/z 538 [MH$^+$].

b. trans-4-{3-[3-(2-Morpholin-4-yl-ethoxy)-phenyl]-[1,2,4]triazolo[4,3-a]pyridin-6-yloxy}-cyclohexylamine trifluoroacetic acid salt

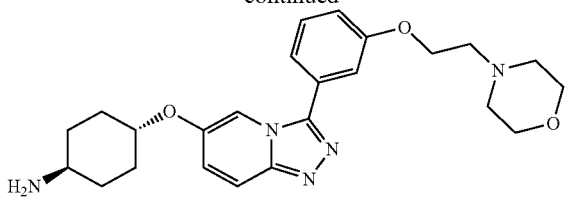

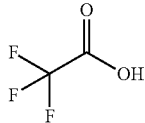

A solution of Example 14 step a (196 mg, 0.178 mmol) in TFA (2 mL) and DCM (10 mL) was stirred at RT for 0.5 H, then concentrated in vacuo to give the title compound (quantitative yield). LCMS (Method 2): Rt 0.38 min, m/z 438 [M-CF$_3$CO$_2^+$].

c. 1-(5-tert-Butyl-2-p-tolyl-2H-pyrazol-3-yl)-3-(trans-4-{3-[3-(2-morpholin-4-yl-ethoxy)-phenyl]-[1,2,4]triazolo[4,3-a]pyridin-6-yloxy}-cyclohexyl)-urea The title compound was prepared in a similar manner to Example 10 step d using Example 14 step b. LCMS (Method 4): Rt 7.84 min, m/z 693 [MH$^+$]. $^1$H NMR (400 MHz, CDCl$_3$): δ 7.76 (1 H, d, J 2), 7.61 (1 H, d, J 9.9), 7.47 (1 H, t, J 8.1), 7.34-7.27 (4 H, m), 7.13 (2 H, d, J 8.1), 7.10-7.03 (2 H, m), 6.86 (1 H, s), 6.28 (1 H, s), 5.49 (1 H, d, J 7.6), 4.19 (2 H, t, J 5.4), 4.06-3.97 (1 H, m), 3.76-3.67 (5 H, m), 2.88 (2 H, t, J 5.4), 2.62 (4 H, t, J 4.4), 2.29 (3 H, s), 2.07 (4 H, d, J 11.4), 1.65-1.53 (2 H, m), 1.33 (9 H, s), 1.29-1.16 (2 H, m).

The following Examples were prepared using similar methods to that used in Example 14:

| Example No. | Structure | NMR (400 MHz) δ | LCMS |
|---|---|---|---|
| 15 | 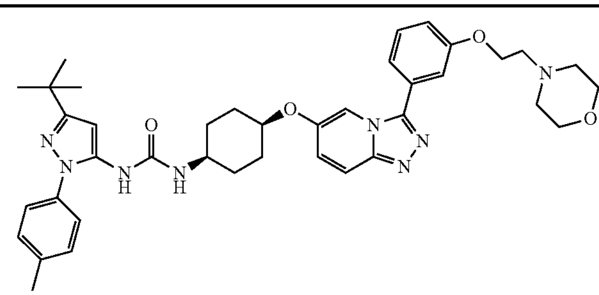 | (CDCl$_3$): 7.75 (1H, d, J 2), 7.69 (1H, d, J 9.9), 7.48 (1H, t, J 7.9), 7.35-7.31 (4H, m), 7.19 (2H, d, J 8), 7.08 (2H, dd, J 9.4, 2.1), 6.49 (1H, s), 6.26 (1H, s), 5.16 (1H, d, J 7.6), 4.35 (1H, m), 4.21 (2H, t, J 5.5), 3.75-3.69 (5H, m), 2.87 (2H, t, J 5.5), 2.63 (4H, m), 2.33 (3H, s), 2.03-1.93 (2H, m), 1.84-1.65 (4H, m), 1.61-1.49 (2H, m), 1.34 (9H, s). | (Method 4): Rt 7.82 min, m/z 693 [MH$^+$]. |
| 16 | 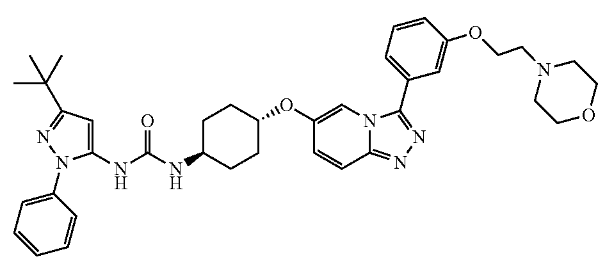 [SMILES: CC(C)(C)c1cc(NC(=O)N[C@H]2CC[C@H](Oc3ccc4nnc(-c5cccc(OCCN6CCOCC6)c5)n4c3)CC2)n(-c2ccccc2)n1] | (CD$_3$OD): 7.92 (1H, d, J 2), 7.72 (1H, d, J 9.9), 7.57-7.47 (3H, m), 7.46-7.37 (5H, m), 7.33 (1H, dd, J 9.9, 2.0), 7.19 (1H, ddd, J 8.3, 2.5, 1.0), 6.32 (1H, s), 4.24 (3H, m), 3.71 (4H, t, J 4.6), 3.58 (1H, m), 2.87 (2H, t, J 5.4), 2.63 (4H, t, J 4.5), 2.16-2.07 (2H, m), 2.03-1.94 (2H, m), 1.64-1.52 (2H, m), 1.45-1.25 (11H, m). | (Method 4): Rt 7.52 min, m/z 679 [MH$^+$]. |

EXAMPLE 17

N-(5-tert-Butyl-2-p-tolyl-2H-pyrazol-3-yl)-2-(4-{3-[3-(2-morpholin-4-yl-ethoxy)-phenyl]-[1,2,4]triazolo[4,3-a]pyridin-6-yloxy}-piperidin-1-yl)-acetamide

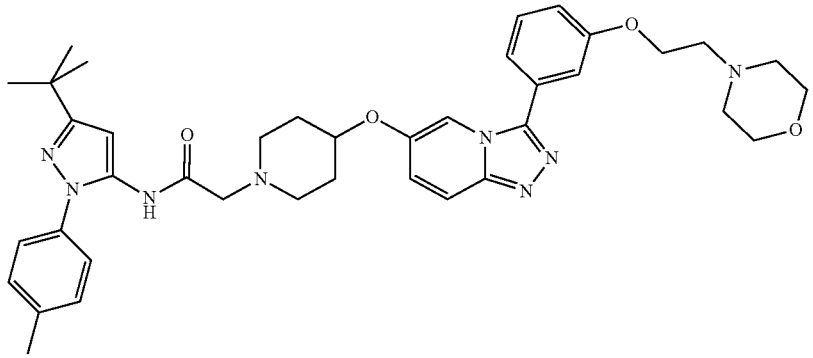 [SMILES: Cc1ccc(-n2nc(C(C)(C)C)cc2NC(=O)CN2CCC(Oc3ccc4nnc(-c5cccc(OCCN6CCOCC6)c5)n4c3)CC2)cc1]

a. 3-[3-(2-Morpholin-4-yl-ethoxy)-phenyl]-6-(piperidin-4-yloxy)-[1,2,4]triazolo[4,3-a]pyridine

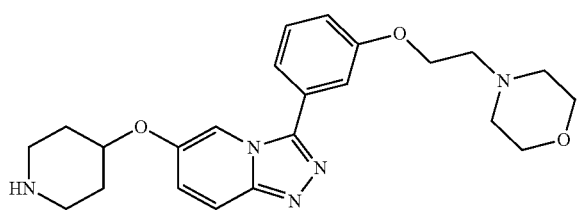 [SMILES: c1cc(OCCN2CCOCC2)cc(-c2nnc3ccc(OC4CCNCC4)cn23)c1]

The title compound was prepared in a similar manner to Example 14 steps a-b, using N-Boc-4-hydroxypiperidine, followed by purification on SCX-2 cartridge. LCMS (Method 5): Rt 0.38, 1.87 min, m/z 424 [MH+].

b. N-(5-tert-Butyl-2-p-tolyl-2H-pyrazol-3-yl)-2-chloro-acetamide

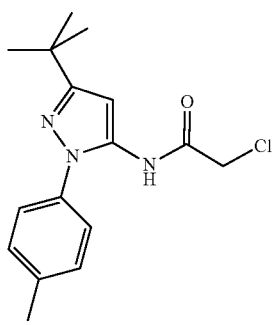 [SMILES: Cc1ccc(-n2nc(C(C)(C)C)cc2NC(=O)CCl)cc1]

A solution of 5-tert-butyl-2-p-tolyl-2H-pyrazol-3-ylamine (886 mg, 3.86 mmol), pyridine (465 µL, 5.80 mmol) and chloroacetyl chloride (462 µL, 5.80 mmol) in DCM (5 mL) was stirred at RT for 2 h. The reaction mixture was diluted with aq. sat. sodium bicarbonate and DCM and the resulting aqueous layer was extracted twice with DCM. The combined organic layers were dried (MgSO4) and concentrated in vacuo to afford the title compound (1.17 g, 100%) as a yellow solid. LCMS (Method 5): Rt 4.41 min, m/z 306 [MH+].

c. N-(5-tert-Butyl-2-p-tolyl-2H-pyrazol-3-yl)-2-(4-{3-[3-(2-morpholin-4-yl-ethoxy)-phenyl]-[1,2,4]triazolo[4,3-a]pyridin-6-yloxy}-piperidin-1-yl)-acetamide A solution of Example 17 step a (32 mg, 0.076 mmol), Example 17 step b (23 mg, 0.076 mmol), potassium iodide (4 mg, 0.002 mmol) and potassium carbonate (13 mg, 0.091 mmol) in acetonitrile (5 mL) was heated to reflux for 2.5 h. The reaction mixture was allowed to cool to RT, concentrated in vacuo and purified twice purified by reverse phase preparative HPLC (Method 6) to afford the title compound (5 mg, 9%) as a white solid. LCMS (Method 4): 6 Rt 6.21 min, m/z 693 [MH+]. ¹H NMR (400 MHz, CD3OD): 7.92 (1 H, d, J 2.0), 7.76 (1 H, d, J 9.9), 7.58 (1 H, t, J 8.1), 7.43-7.32 (7 H, m), 7.22 (1 H, dd, J 8.4, 2.3), 6.51 (1 H, s), 4.36-4.29 (1 H, m), 4.26 (2 H, t, J 5.4), 3.72 (4 H, t, J 4.6), 3.10 (2 H, s), 2.89 (2 H, t, J 5.4), 2.72-2.62 (6 H, m), 2.44-2.32 (5 H, m), 1.85 (2 H, m), 1.61-1.53 (2 H, m), 1.33 (9 H, s).

EXAMPLE 18

N-(5-tert-Butyl-2-p-tolyl-2H-pyrazol-3-yl)-2-{4-[3-(3-hydroxy-phenyl)-[1,2,4]triazolo[4,3-a]pyridin-6-ylsulfanyl]-phenyl}-acetamide

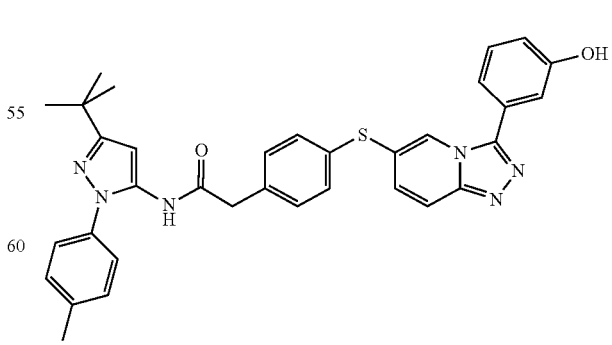

The title compound was prepared in a similar manner to Example 10 step a using Example 8. LCMS (Method 7): Rt 12.01 min, m/z 589 [MH+]. ¹H NMR (400 MHz, CD₃OD): δ 8.35 (1 H, t, J 1.2), 7.74 (1 H, dd, J 9.6, 1.0), 7.45-7.36 (1 H, m), 7.37-7.32 (3 H, m), 7.24-7.20 (4 H, m), 7.25-7.07 (4 H, m), 6.99 (1 H, ddd, J 8.2, 2.4, 1.1), 6.32 (1 H, s), 3.58 (2 H, s), 2.31 (3 H, s), 1.31 (9 H, s).

EXAMPLE 19

N-{5-tert-Butyl-2-[4-(2-morpholin-4-yl-ethoxy)-phenyl]-2H-pyrazol-3-yl}-2-[4-(3-isopropyl-[1,2,4]triazolo[4,3-a]pyridin-6-ylsulfanyl)-phenyl]-acetamide

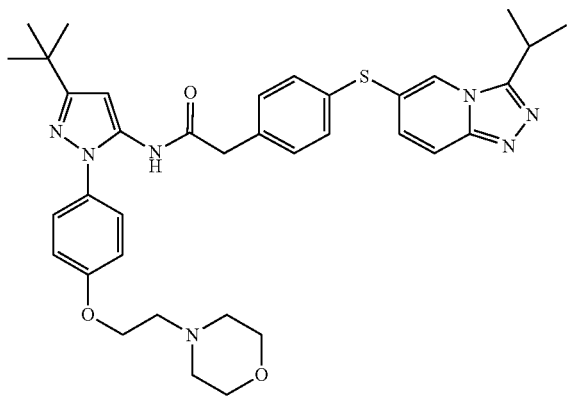 [SMILES: CC(C)c1nnc2ccc(Sc3ccc(CC(=O)Nc4cc(C(C)(C)C)nn4-c4ccc(OCCN5CCOCC5)cc4)cc3)cn12]

a. 5-tert-Butyl-2-[4-(2-morpholin-4-yl-ethoxy)-phenyl]-2H-pyrazol-3-ylamine

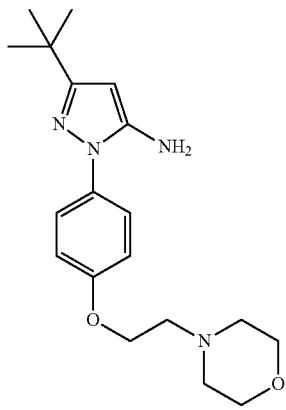 [SMILES: CC(C)(C)c1cc(N)n(-c2ccc(OCCN3CCOCC3)cc2)n1]

A solution of 4-(5-amino-3-tert-butyl-pyrazol-1-yl)-phenol (WO2005/110994, 0.462 g, 2 mmol), 2-morpholin-4-yl-ethanol (0.327 g, 2.5 mmol) and triphenylphosphine (1.05 g, 4 mmol) in THF (5 mL) under a nitrogen atmosphere was treated with diisopropyl azodicarboxylate (0.808 mg, 4 mmol). The reaction mixture was stirred at RT for 16 H, then diluted with diethyl ether. The organic layer was washed with water. The resulting aqueous layer was basified with potassium carbonate and extracted with EtOAc. The resulting organic layer was washed with aq. citric acid solution, and the resulting aqueous layer was basified with potassium carbonate, and extracted with EtOAc (three times). The resulting organic layer was dried (Na₂SO₄), evaporated to dryness then sonicated with diethyl ether (10 mL) and filtered to give the title compound (0.297 g, 43%) as a white solid. LCMS (Method 5): Rt 0.41, 2.16 min, m/z 345 [MH+]. ¹H NMR (400 MHz, CDCl₃): δ 7.46-7.39 (2 H, m), 6.98-6.93 (2 H, m), 5.50 (1 H, s), 4.15-4.08 (2 H, m), 3.75 (4 H, t, J 4.5), 3.63 (2 H, bs), 2.83-2.78 (2 H, m), 2.59 (4 H, t, J 4.3), 1.34-1.26 (9 H, m).

b. N-{5-tert-Butyl-2-[4-(2-morpholin-4-yl-ethoxy)-phenyl]-2H-pyrazol-3-yl}-2-(4-(3-isopropyl-[1,2,4]-triazolo[4,3-a]pyridin-6-ylsulfanyl)-phenyl]-acetamide The title compound was prepared in a similar manner to Example 1 steps c-d, using 3-mercaptoacetic acid and Example 19 step a. LCMS (Method 7): Rt 9.09 min, m/z 654 [MH+]. ¹H NMR (400 MHz, CDCl₃): 8.12 (1 H, s), 7.70 (1 H, d, J 9.6), 7.22 (2 H, d, J 8.0), 7.20-7.09 (5 H, m), 7.12-7.05 (1 H, m), 6.93-6.86 (2 H, m), 6.57 (1 H, s), 4.17 (2 H, t, J 5.7), 3.73 (4 H, t, J 4.5), 3.64 (2 H, s), 3.41-3.32 (1 H, m), 2.84 (2 H, t, J 5.7), 2.59 (4 H, t, J 4.4), 1.56 (3 H, s), 1.54 (3 H, s), 1.32 (9 H, s).

EXAMPLE 20

N-[5-tert-Butyl-2-(4-hydroxy-phenyl)-2H-pyrazol-3-yl]-2-[4-(3-isopropyl-[1,2,4]triazolo[4,3-a]pyridin-6-ylsulfanyl)-phenyl]-acetamide

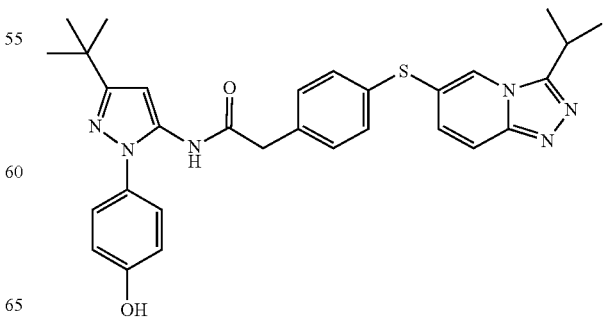

a. N-{5-tert-Butyl-2-[4-(tert-butyl-dimethyl-silanyloxy)-phenyl]-2H-pyrazol-3-yl}-2-[4-(3-isopropyl-[1,2,4]triazolo[4,3-a]pyridin-6-ylsulfanyl)-phenyl]-acetamide

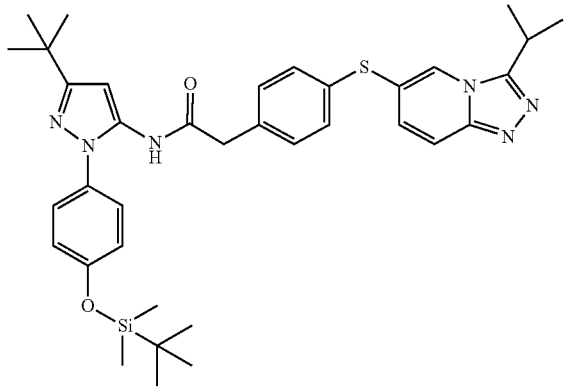 [SMILES: CC(C)c1nnc2ccc(Sc3ccc(CC(=O)Nc4cc(C(C)(C)C)nn4-c4ccc(O[Si](C)(C)C(C)(C)C)cc4)cc3)cn12]

The title compound was prepared in a similar manner to Example 19 step b, using 5-tert-butyl-2-[4-(tert-butyl-dimethyl-silanyloxy)-phenyl]-2H-pyrazol-3-ylamine (US2006/035922). LCMS (Method 5): Rt 4.96 min, m/z 655 [MH⁺]. $^1$H NMR (300 MHz, CD$_3$OD): δ 8.47 (1 H, s), 7.65 (1 H, dd, J=9.60, 1.01 Hz), 7.35-7.24 (3 H, m), 7.22-7.17 (4 H, m), 6.89-6.84 (2 H, m), 6.30 (1 H, s), 3.59 (2 H, s), 2.99 (1 H, m), 1.48 (3 H, s), 1.45 (3 H, s), 1.30 (9 H, s), 0.99 (9 H, s), 0.20 (6 H, s).

b. N-[5-tert-Butyl-2-(4-hydroxy-phenyl)-2H-pyrazol-3-yl]-2-[4-(3-isopropyl-[1,2,4]triazolo[4,3-a]pyridin-6-ylsulfanyl)-phenyl]-acetamide A solution of Example 20 step a (80 mg, 0.12 mmol) and triethylamine trihydrofluoride (40 mg, 0.24 mmol) in THF (2 mL) was stirred at RT for 24 H, then diluted with EtOAc, washed with sat. aq. sodium bicarbonate, dried (Na$_2$SO$_4$), and evaporated. The residue was purified by FCC (DCM/MeOH 100/0 to 95/5), dissolved in EtOAc, washed with aq. citric acid and brine, dried (Na$_2$SO$_4$), evaporated and dried in vacuo at 40° C. to afford the title compound (45 mg, 68%) as a pink solid. LCMS (Method 7): Rt 11.15 min, m/z 541 [MH⁺]. $^1$H NMR (400 MHz, CDCl$_3$): δ 8.23 (1 H, s), 7.91 (1 H, s), 7.74 (1 H, d, J 9.5), 7.25-7.14 (5 H, m), 7.05 (2 H, d, J 8.4), 6.85 (2 H, t, J 8.6), 6.51 (1 H, s), 3.64 (2 H, s), 3.47-3.38 (1 H, m), 1.55 (3 H, s), 1.53 (3 H, s), 1.31 (9 H, s).

EXAMPLE 21

1-(5-tert-Butyl-2-p-tolyl-2H-pyrazol-3-yl)-3-[4-(3-isopropyl-[1,2,4]triazolo[4,3-a]pyridin-6-yloxy)-cyclohexyl]-urea

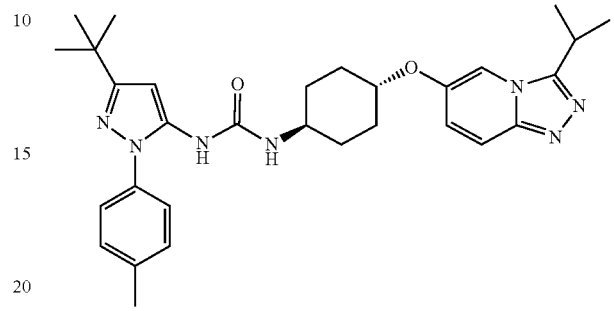

a. Isobutyric acid N'-(5-fluoro-pyridin-2-yl)-hydrazide

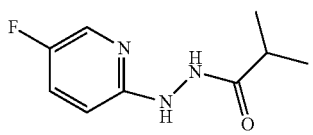

A solution of 5-fluoro-2-hydrazinyl-pyridine (0.59 g, 4.65 mmol), isobutyric acid (528 mg, 6 mmol), and HOBt hydrate (153 mg, 1 mmol) in DCM (10 mL) was treated with EDCl HCl (1.15 g, 6 mmol). The reaction mixture was stirred at RT for 40 min, poured onto sat. aq. sodium bicarbonate (40 mL), extracted with four portions of DCM, dried (Na$_2$SO$_4$), evaporated and purified by FCC (DCM/EtOAc 9/1 to 3/7) to give the title compound (0.42 g, 46%). LCMS (Method 8): Rt 2.46 min, m/z 198 [MH⁺].

b. 6-Fluoro-3-isopropyl-[1,2,4]triazolo[4,3-a]pyridine

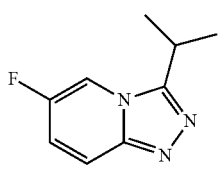

A solution of Example 21 step a (0.41 g, 2.08 mmol), triphenylphosphine (763 mg, 2.91 mmol) and triethylamine (0.87 mL, 6.24 mmol) in THF (5 mL) at 0° C. was treated with 1,2-hexachloroethane (690 mg, 2.91 mmol). The reaction mixture was stirred at 0° C. for 40 min then at RT for 20 min, quenched with water, extracted twice with EtOAc, dried (Na$_2$SO$_4$), evaporated and purified twice by FCC (cyclohexane/EtOAc 1/0 to 1/1) to afford the title compound (274 mg, contaminated with 20% PPh₃O, 58%) as a white solid. LCMS (Method 5): Rt 2.58 min, m/z 180 [MH⁺].

c. 4-(3-Isopropyl-[1,2,4]-triazolo[4,3-a]pyridin-6-yloxy)-cyclohexylamine

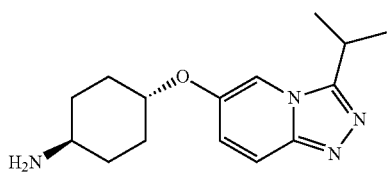

A solution of trans-4-amino-cyclohexanol (402 mg, 3.6 mmol) and potassium tert-butoxide (395 mg, 3.6 mmol) in toluene (1 mL) and 1,3-dimethyl-3,4,5,6-tetrahydro-2(1H)-pyrimidinone (0.5 mL) was heated at 80° C. under argon for 20 min, then treated with Example 21 step b (274 mg, contaminated with 20% PPh₃O, 1.2 mmol). The reaction mixture was stirred for 1 H, quenched with water and extracted with three portions of EtOAc. The aqueous and the combined organic layers were purified on SCX cartridge (MeOH to 1N NH₃ in MeOH), and the resulting residue was purified by FCC (DCM/MeOH with 0.1% NH₃ 100/0 to 85/15) to give the title compound (235 mg, 71%). LCMS (Method 5): Rt 1.86 min, m/z 275 [MH⁺].

d. 1-(5-tert-Butyl-2-p-tolyl-2H-pyrazol-3-yl)-3-[4-(3-isopropyl-[1,2,4]triazolo[4,3-a]pyridin-6-yloxy)-cyclohexyl]-urea The title compound was prepared in a similar manner to Example 10 step d starting from Example 21 step c and using dioxane in place of DMSO. LCMS (Method 7): Rt 11.66 min, m/z 530 [MH⁺]. ¹H NMR (400 MHz, CDCl₃): δ 7.60 (1 H, d, J 9.9), 7.37 (1 H, s), 7.34 (2 H, d, J 8.2), 7.19 (2 H, d, J 8.1), 7.03 (1 H, dd, J 9.9, 2.0), 6.37 (1 H, s), 6.23 (1 H, s), 5.12 (1 H, d, J 7.5), 4.07 (1 H, m), 3.73 (1 H, m), 3.31-3.22 (1 H, m), 2.34 (3 H, s), 2.12-2.05 (4 H, m), 1.68-1.56 (2 H, m), 1.51 (3 H, s), 1.49 (3 H, s), 1.54-1.31 (2 H, m), 1.34 (9 H, s).

EXAMPLE 22

N-(5-tert-Butyl-2-p-tolyl-2H-pyrazol-3-yl)-2-[4-(3-isopropyl-[1,2,4]-triazolo[4,3-a]pyridin-6-yloxy)-cyclohexyl]-acetamide

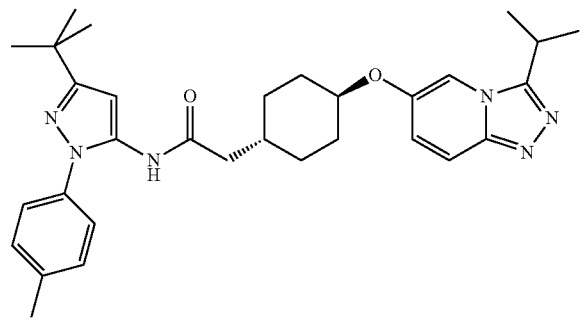 [SMILES: Cc1ccc(-n2nc(C(C)(C)C)cc2NC(=O)C[C@H]2CC[C@H](Oc3ccc4nnc(C(C)C)n4c3)CC2)cc1]

a. [4-(3-Isopropyl-[1,2,4]triazolo[4,3-a]pyridin-6-yloxy)-cyclohexyl]-acetic acid ethyl ester

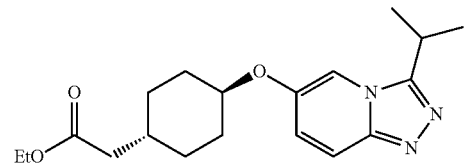 [SMILES: CCOC(=O)C[C@H]1CC[C@H](Oc2ccc3nnc(C(C)C)n3c2)CC1]

The title compound was prepared in a similar manner to Example 21 step c starting from trans-(4-hydroxy-cyclohexyl)-acetic acid ethyl ester (Krieg et al., *Journal fuer Praktische Chemie* 1987, 329 (6), 1123-30)). LCMS (Method 5): Rt 4.16-423 min, m/z 346 [MH⁺].

b. [4-(3-Isopropyl-[1,2,4]-triazolo[4,3-a]pyridin-6-yloxy)-cyclohexyl]-acetic acid

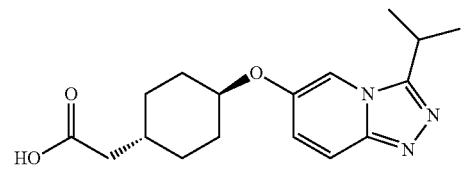 [SMILES: CC(C)c1nnc2ccc(O[C@H]3CC[C@H](CC(=O)O)CC3)cn12]

A solution of Example 22 step a (50 mg, 0.145 mmol) and 1N sodium hydroxide (0.5 mL, 0.5 mmol) in MeOH (2 mL) was stirred at RT for 16 h. The reaction mixture was treated with sat. aq. sodium bicarbonate, evaporated to dryness, and purified on a reverse phase FCC (water/MeOH 100/0.0 to 0/100) to give two fractions. The first eluting fraction was acidified to pH 5 with 1N HCl solution and extracted with EtOAc. The organic layer was dried (MgSO₄), filtered, combined with the second eluting fraction from chromatography and concentrated in vacuo. The resulting residue was dissolved in MeOH/EtOAc (1:1, 10 mL), filtered and evaporated to dryness to give the title compound as a pale brown solid (27 mg, 59%). LCMS (Method 5): Rt 3.58-3.65 min, m/z 318 [MH⁺].

c. N-(5-tert-Butyl-2-p-tolyl-2H-pyrazol-3-yl)-2-[4-(3-isopropyl-[1,2,4]triazolo[4,3-a]pyridin-6-yloxy)-cyclohexyl]-acetamide The title compound was prepared in a similar manner to Example 1 step d starting from Example 22 step b. LCMS (Method 10): Rt 11.59 min, m/z 529 [MH⁺]. ¹H NMR (400 MHz, CDCl₃): δ 7.67 (1 H, d, J 9.9), 7.38 (1 H, s), 7.36-7.25 (4 H, m), 7.20 (1 H, m), 7.04 (1 H, dd, J 9.8, 2.0), 6.60 (1 H, s), 4.10-3.98 (1 H, m), 3.3.28 (1 H, m), 2.41 (3 H, s), 2.21 (2 H, d, J 6.5), 2.16 (3 H, m), 1.93 (4 H, m), 1.52 (3 H, s), 1.51 (3 H, s), 1.34 (9 H, s), 1.23-1.07 (2 H, m).

EXAMPLE 23

N-(5-tert-Butyl-2-p-tolyl-2H-pyrazol-3-yl)-2-[4-(3-isopropyl-[1,2,4]triazolo[4,3-a]pyridin-6-yloxy)-phenyl]-acetamide

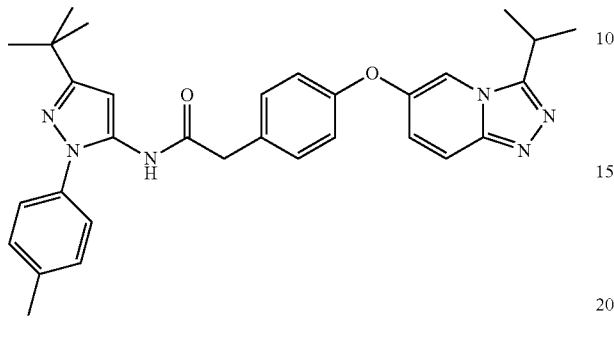

a. 6-Iodo-3-isopropyl-[1,2,4]triazolo[4,3-a]pyridine

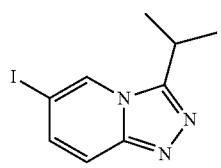

The title compound was prepared in a similar manner to Example 1 steps a-b using 2-methyl-propionaldehyde. LCMS (Method 5): Rt 3.43 min, m/z 288 [MH$^+$]. $^1$H NMR (300 MHz, CD$_3$OD): 8.75 (1 H, s), 7.58 (1 H, dd, J 9.6, 1.5), 7.52 (1 H, dd, J 9.6, 1.1), 3.68-3.49 (1 H, m), 1.50 (3 H, s), 1.47 (3 H, s).

b. 2-[4-(3-Isopropyl-[1,2,4]triazolo[4,3-a]pyridin-6-yloxy)-phenyl]-acetamide

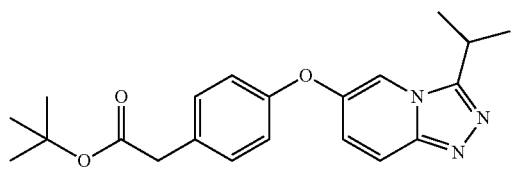 [SMILES: CC(C)c1nnc2ccc(Oc3ccc(CC(=O)OC(C)(C)C)cc3)cn12]

A solution of Example 23 step a (430 mg, 1.5 mmol), tert-butyl 2-(4-hydroxyphenyl)acetate (WO2008/024746, 621 mg, 3 mmol), cesium carbonate (978 mg, 3 mmol), copper (I) chloride (74 mg, 0.75 mmol) and 2,2,6,6-tetramethyl-heptanedione (28 mg, 0.15 mmol) in N-methylpyrrolidinone (2 mL) was heated at 115° C. for 1 h. The reaction mixture was left to cool to RT, diluted with diethyl ether and washed with water. The aqueous layer was extracted with EtOAc and DCM and the combined organic layers were dried (Na$_2$SO$_4$), filtered and concentrated in vacuo. The resulting oil was purified on a SCX-2 cartridge eluting with EtOAc, MeOH then 1N ammonia in MeOH. The ammonia fractions were concentrated in vacuo and purified twice by FCC (DCM/MeOH containing NH$_3$ 10/0 to 9/1 then EtOAc) to provide the title compound as an orange gum (44 mg, 8%). LCMS (Method 8): Rt 4.30 min, m/z 368 [MH$^+$].

c. [4-(3-Isopropyl-[1,2,4]triazolo[4,3-a]pyridin-6-yloxy)-phenyl]-acetic acid

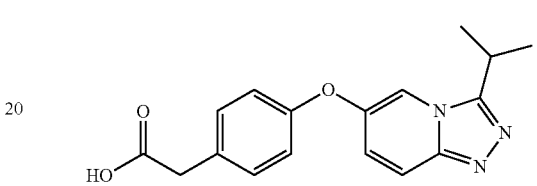

A solution of Example 23 step b (44 mg, 0.12 mmol), TFA (1 mL) and anisole (1 mL) in DCM (1 mL) was stirred at RT for 1 H, then evaporated in vacuo. The resulting residue was suspended in diethyl ether (3 mL), filtered and dried in vacuo to give the title compound (38 mg, quant.). LCMS (Method 5): Rt 3.65 min, m/z 312 [MH$^+$].

d. N-(5-tert-Butyl-2-p-tolyl-2H-pyrazol-3-yl)-2-[4-(3-isopropyl-[1,2,4]triazolo[4,3-a]pyridin-6-yloxy)-phenyl]-acetamide The title compound was prepared in a similar manner to Example 1 step d starting from Example 23 step c. LCMS (Method 10): Rt 11.60 min, m/z 523 [MH$^+$]. $^1$H NMR (400 MHz, CDCl$_3$): 7.77 (1 H, d, J 9.9), 7.66 (1 H, s), 7.29 (1 H, s), 7.26-7.15 (4 H, m), 7.14 (2 H, d, J 8.1), 7.05 (1 H, dd, J 9.9, 2.0), 6.98 (2 H, d, J 8.1), 6.60 (1 H, s), 3.67 (2 H, s), 3.27 (1 H, m), 2.39 (3 H, s), 1.52 (3 H, s), 1.50 (3 H, s), 1.33 (9 H, s).

EXAMPLE 24

N-(5-tert-Butyl-2-p-tolyl-2H-pyrazol-3-yl)-2-[4-(3-isopropyl-[1,2,4]triazolo[4,3-a]pyridin-6-ylsulfanyl)-phenyl]-propionamide

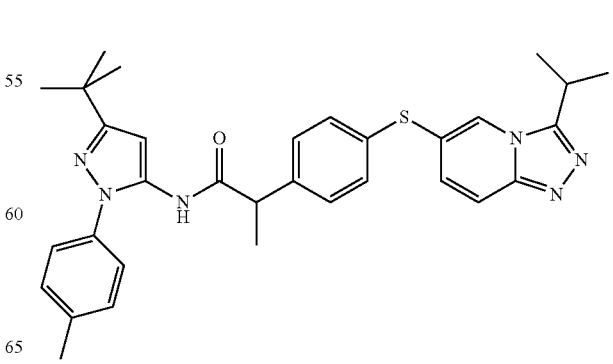

a. [4-(3-Isopropyl-[1,2,4]-triazolo[4,3-a]pyridin-6-ylsulfanyl)-phenyl]-acetic acid methyl ester

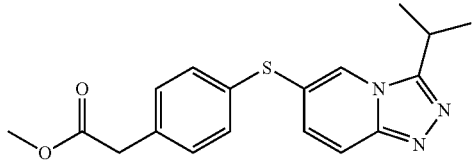 [SMILES: COC(=O)Cc1ccc(Sc2ccc3nnc(C(C)C)n3c2)cc1]

To a solution of 4-(3-isopropyl-[1,2,4]triazolo[4,3-a]pyridin-6-ylsulfanyl)-phenyl]-acetic acid (prepared in a similar manner to Example 1 step c) (209 mg, 0.639 mmol) in MeOH (20 mL) was added concentrated HCl (25 μL) and the reaction stirred at reflux for 5 h. The reaction was cooled to RT, concentrated in vacuo, partitioned between DCM (5 mL) and sat. NaHCO$_3$ (5 mL), the organic layer was separated, dried (MgSO$_4$), and concentrated in vacuo to afford the title compound (218 mg). LCMS (Method 1): Rt 3.04 min, m/z 342 [MH$^+$].

b. 2-[4-(3-Isopropyl-[1,2,4]triazolo[4,3-a]pyridin-6-ylsulfanyl)-phenyl]-propionic acid methyl ester

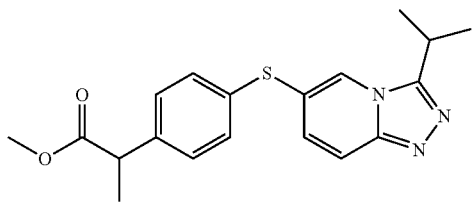 [SMILES: COC(=O)C(C)c1ccc(Sc2ccc3nnc(C(C)C)n3c2)cc1]

A solution of the product from Example 24 step b (218 mg, 0.637 mmol) in THF (5 mL) was cooled to 0° C. and LiHMDS (1M in hexanes, 702 μL, 0.702 mmol) was added. After 10 min. iodomethane (43 μL, 0.702 mmol) was added and stirring continued at 0° C. for 0.5 h, then slowly allowed to warm to RT with stirring overnight. The reaction was quenched with sat. NH$_4$Cl solution (5 mL), extracted with Et$_2$O (2×10 mL), dried (MgSO$_4$), and concentrated in vacuo. Purification by chromatography using 0-10% DCM/MeOH gave the title compound (69.2 mg, 30%). LCMS (Method 1): Rt 3.25 min, m/z 356 [MH$^+$].

c. 2-[4-(3-Isopropyl-[1,2,4]triazolo[4,3-a]pyridin-6-ylsulfanyl)-phenyl]-propionic acid

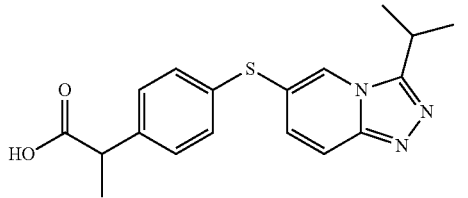 [SMILES: CC(C)c1nnc2ccc(Sc3ccc(C(C)C(=O)O)cc3)cn12]

A solution of the product from Example 24 step c (69.2 mg, 0.194 mmol) in 1 M NaOH (1 mL) and MeOH (2 mL) was stirred at room temperature for 3.5 h. The reaction was quenched with acetic acid (1 mL) and concentrated in vacuo to afford the title compound. LCMS (Method 1): Rt 3.11 min, m/z 342 [MH$^+$].

d. N-(5-tert-Butyl-2-p-tolyl-2H-pyrazol-3-yl)-2-[4-(3-isopropyl-[1,2,4]triazolo[4,3-a]pyridin-6-ylsulfanyl)-phenyl]-propionamide The title compound was prepared in a similar manner to Example 1 step d starting from Example 24 step c. LCMS (Method 4): Rt 5.25 min, m/z 553 [MH$^+$]. $^1$H NMR (400 MHz, MeOD): δ 8.53 (1 H, dd, J 1.6, 1.0 Hz), 7.66 (1 H, dd, J 9.5, 1.0 Hz), 7.34 (2 H, m), 7.31 (1 H, dd, J 9.5, 1.6 Hz), 7.23 (2 H, m), 7.09 (4 H, s), 6.27 (1 H, s), 3.72 (1 H, q, J 7.1 Hz), 3.55 (1 H, m), 2.31 (3 H, s), 1.47 (6 H, 2×d, J 6.9 Hz), 1.40 (3 H, d, J 7.1 Hz), 1.30 (9 H, s).

EXAMPLE 25

1-(5-tert-Butyl-2-p-tolyl-2H-pyrazol-3-yl)-3-[4-(3-cyclopentyl-[1,2,4]triazolo[4,3-a]pyridin-6-yloxy)-cyclohexyl]-urea

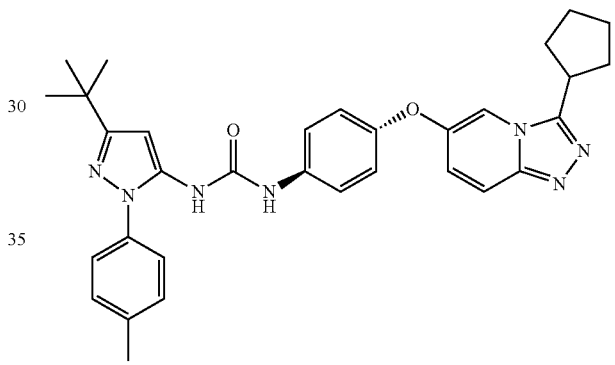

The title compound was prepared in a similar manner to Example 21. LCMS (Method 11): Rt 4.59 min, m/z 555 [M$^+$]. $^1$H NMR (400 MHz, MeOD): δ 7.88 (1 H, dd, J 2.1, 0.8), 7.60 (1 H, dd, J 9.9, 0.8), 7.30 (4 H, m), 7.25 (1 H, dd, 9.9, 2.1), 6.27 (1 H, s), 4.32 (1 H, m), 3.57 (2 H, m), 2.38 (3 H, s), 2.20 (2 H, m), 2.10 (2 H, m), 1.87 (9 H, m), 1.56 (2 H, m), 1.35 (1 H, m), 1.28 (9 H, s).

EXAMPLE 26

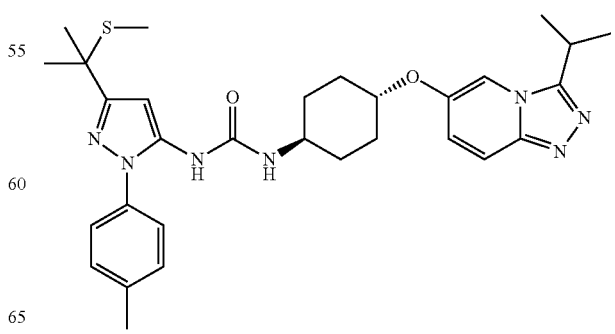

1-[4-(3-Isopropyl-[1,2,4]-triazolo[4,3-a]pyridin-6-yloxy)-cyclohexyl]-3-[5-(1-methyl-1-methylsulfanyl-ethyl)-2-p-tolyl-2H-pyrazol-3-yl]-urea The title compound was prepared in a similar manner to Example 1 step d starting from Example 21 step c. LCMS (Method 11): Rt 4.59 min, m/z 561 [M+]. $^1$H NMR (400 MHz, MeOD): δ 7.85 (1H, dd, J 2.1, 0.8), 7.57 (1 H, dd, J 9.9, 0.8), 7.30 (4 H, m), 7.21 (1 H, dd, 9.9, 2.1), 6.41 (1 H, s), 4.32 (1 H, m), 3.56 (1 H, m), (1 H, sept., J 6.9), 2.38 (3 H, s), 2.11 (2 H, m), 1.98 (2 H, m), 1.91 (3 H, s), 1.61 (6 H, s), 1.56 (2 H, m), 1.42 (6 H, d, J 6.9), 1.35 (3 H, m).

EXAMPLE 27

N-{5-tert-Butyl-2-[3-(2-pyridin-4-yl-ethoxy)-phenyl]-2H-pyrazol-3-yl}-2-[4-(3-isopropyl-[1,2,4]triazolo[4,3-a]pyridin-6-ylsulfanyl)-phenyl]-acetamide

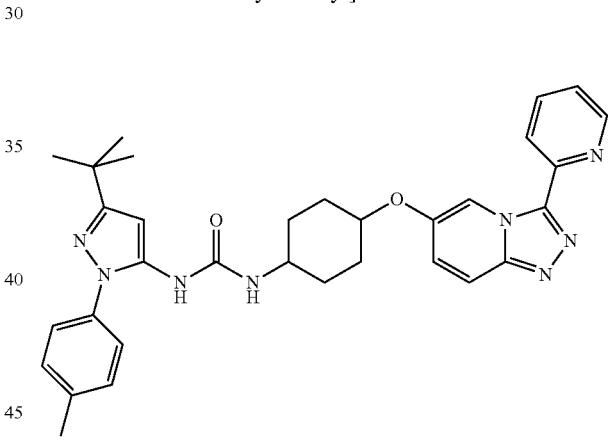

The title compound was prepared in a similar manner to Example 1 step d. LCMS (Method 11): Rt 3.81 min, m/z 646 [MH+]. $^1$H NMR (400 MHz, CDCl$_3$): δ 8.53-8.49 (2 H, m), 8.04 (1 H, s), 7.64 (1 H, d, J 9.6), 7.26 (1 H, s NH), 7.24-7.10 (7 H, m), 7.02 (1 H, dd, J 9.6, 1.6), 6.87 (1 H, t, J 2.4), 6.82 (1 H, ddd, J 8.4, 2.4, 1.0), 6.63 (1 H, d, J 7.9), 6.57 (1 H, s), 4.19 (2 H, t, J 6.4), 3.62 (2 H, s), 2.36-3.28 (1 H, m), 3.08 (2 H, t, J 6.4), 1.51 (6 H, d, 6.9), 1.29 (9 H, s).

EXAMPLE 28

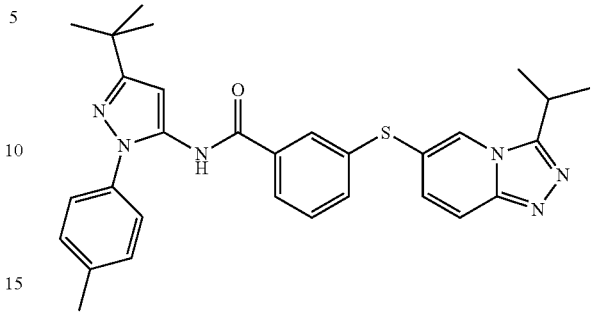

Example 28 was prepared using similar method to that used in Example 1. LCMS (Method 11): Rt 5.12 min, m/z 525 [MH+]. $^1$H NMR (400 MHz, CDCl$_3$): δ 1.36 (9H, s), 1.54 (6H, d, J 8 Hz), 2.41 (3H, s), 3.37 (1H, q, J 8 Hz), 6.71 (1H, s), 7.12-7.16 (1H, m), 7.28-7.33 (2H, m), 7.35-7.46 (5H, m), 6.68-7.73 (1H, m), 7.78 (1H, s), 7.91 (1H, s), 8.12 (1H, s).

EXAMPLE 29

1-(5-tert-Butyl-2-p-tolyl-2H-pyrazol-3-yl)-3-[4-(3-pyridin-2-yl-[1,2,4]triazolo[4,3-a]pyridin-6-yloxy)-cyclohexyl]-urea The title compound was prepared in a similar manner to Example 10 step d using dioxane in place of DMSO and heating at 80° C. LCMS (Method 7): Rt 4.95 min, m/z 565 [MH+]. $^1$H NMR (400 MHz, DMSO): δ. 9.36 (1 H, dd, J 2.3, 0.8), 8.74 (1 H, ddd, J 4.9, 1.8, 1.1), 8.34 (1 H, dt, J 8.1, 1.1, 1.1), 8.03-7.97 (1 H, m), 7.91 (1 H, s, NH), 7.86 (1 H, dd, J 9.8, 0.8), 7.48 (1 H, ddd, J 7.5, 4.9, 1.1), 7.37 (1 H, dd, J 9.8, 2.3), 7.31-7.24 (4 H, m), 6.52 (1 H, d, J 7.4 NH), 6.21 (1 H, s), 4.34-4.24 (1 H, m), 3.52-3.40 (1 H, m), 2.32 (3 H, s), 2.12-2.00 (2 H, m), 1.92-1.84 (2 H, m), 1.56-1.44 (2 H, m), 1.34-1.22 (2 H, m), 1.20 (9 H, s).

Biological Assays
p38 Kinase Assay

Human recombinant p38 enzyme expressed in *E. coli* and activated by incubation with MKK6 enzyme (Calbiochem #559324) is used as source of enzyme activity.

The assay is carried in high binding, clear, flat bottom 96 well assay plates which have been coated with recombinant ATF-2 (Biosource #PHF0043). Test compounds are incubated with p38 kinase for 2 h prior to initiating the kinase assay by the addition of ATP to obtain an assay concentration of 250 μM. Phosphorylation of ATF-2 is detected and quantified using an ELISA. This consists of sequential incubation in the presence of anti-phospho-ATF2, biotinylated anti-IgG and streptavidin-HRP. Incubation with an HRP chromogenic substrate (TMB) results in absorbance that is proportional to the amount of phosphorylated substrate produced. Absorbance is detected using a multiwell plate reader.

Compounds are diluted in DMSO prior to addition to assay buffer, the final DMSO concentration in the assay being 1%.

The $IC_{50}$ is defined as the concentration at which a given compound achieves 50% inhibition of control.

Results are shown in Table 1:

TABLE 1

| Example | p38α inhibition |
|---|---|
| Example 1 | + |
| Example 2 | ++ |
| Example 3 | ++ |
| Example 4 | ++++ |
| Example 5 | ++ |
| Example 6 | ++++ |
| Example 7 | ++++ |
| Example 8 | +++ |
| Example 9 | +++ |
| Example 10 | +++ |
| Example 11 | + |
| Example 12 | +++ |
| Example 13 | ++ |
| Example 14 | +++ |
| Example 15 | ++ |
| Example 16 | +++ |
| Example 17 | + |
| Example 18 | ++++ |
| Example 19 | + |
| Example 20 | +++ |
| Example 21 | +++ |
| Example 22 | + |
| Example 23 | ++++ |
| Example 24 | ++ |
| Example 25 | ++++ |
| Example 26 | +++ |
| Example 27 | +++ |
| Example 28 | +++ |
| Example 29 | +++ |

In Table 1 above, p38α binding potencies ($IC_{50}$ values) are indicated as follows:
<2000-500 nM '+';
<500-100 nM '++';
10-<100 nM '+++';
<10 nM '++++'.
All compounds tested exhibited $IC_{50}$ values <2000 nM;
NT not tested.

p38 Functional Assay

Inhibition of cellular p38 depresses the release of TNFα, a functional response which is quantified by measurement of the amount of TNFα in the supernatants of LPS activated THP-1 cells (an immortalised monocytic cell line) or peripheral blood mononuclear cells (PBMC's) isolated from freshly drawn human blood.

Cells seeded in 96 well plates are pre-treated by the addition of p38 inhibitors for 1 h followed by addition of lipopolysaccharide (LPS) to activate cytokine production and release. The amount of TNFα released into the cell supernatants is quantified using an R&D Systems enzyme linked immunosorbant assay (ELISA) kit (product DY210) following the manufacturers instructions.

Compounds are diluted in DMSO prior to addition, the final DMSO concentration in the assay being 0.3%. The $EC_{50}$ is defined as the concentration at which a given compound achieves 50% inhibition of the control.

Results are shown in Table 2:

TABLE 2

| Example | $EC_{50}$ |
|---|---|
| Example 1 | + |
| Example 2 | ++ |
| Example 3 | +++ |
| Example 4 | +++ |
| Example 5 | ++ |
| Example 6 | +++ |
| Example 7 | ++++ |
| Example 8 | ++ |
| Example 9 | + |
| Example 10 | +++ |
| Example 11 | ++ |
| Example 12 | +++ |
| Example 13 | +++ |
| Example 14 | +++ |
| Example 15 | + |
| Example 16 | + |
| Example 17 | + |
| Example 18 | +++ |
| Example 19 | + |
| Example 20 | +++ |
| Example 21 | +++ |
| Example 22 | + |
| Example 23 | ++++ |
| Example 24 | NT |
| Example 25 | NT |
| Example 26 | NT |
| Example 27 | NT |
| Example 28 | NT |
| Example 29 | NT |

In Table 2 above, $EC_{50}$ values are indicated as follows:
<7000-500 nM '+';
<500-100 nM '++';
10-<100 nM '+++';
<10 nM '++++'.
All compounds tested exhibited $EC_{50}$ values <2000 nM;
NT not tested.

Biological Assays

Pre-clinical mouse model of COPD inflammation—Tobacco smoke induced pulmonary inflammation.

Previous studies have established that the number of inflammatory cells recovered in the bronchoalveolar lavage (BAL) is significantly elevated 24 h following the final Tobacco Smoke (TS) exposure of 4 or 11 consecutive daily TS exposures, this time point was used in the studies reported here.

Protocols for the exposure of mice to TS, obtaining bronchoalveolar lavage (BAL), preparation of cytospin slides for differential cell counts are as outlined below.

Exposure of Mice to TS Daily for 4 or 11 Consecutive Days

In this exposure protocol, mice were exposed in groups of 5 in individual clear polycarbonate chambers (27 cm×16 cm×12 cm). The TS from the cigarettes was allowed to enter the exposure chambers at a flow rate of 100 ml/min. In order to minimise any potential problems caused by repeated exposure to a high level of TS (6 cigarettes), the exposure of the mice to TS was increased gradually over the exposure period to a maximum of 6 cigarettes. The exposure schedule used for 4 days was as follows:

Day 1: 4 cigarettes (approximately 32 min exposure)
Day 2: 4 cigarettes (approximately 32 min exposure)
Day 3: 6 cigarettes (approximately 48 min exposure)
Day 4: 6 cigarettes (approximately 48 min exposure)

The exposure schedule used for 11 days exposure was as follows:

Day 1: 2 cigarettes (approximately 16 min exposure)
Day 2: 3 cigarettes (approximately 24 min exposure)
Day 3: 4 cigarettes (approximately 32 min exposure)

Day 4: 5 cigarettes (approximately 40 min exposure)

Day 5 to 11: 6 cigarettes (approximately 48 min exposure)

A further group of mice were exposed to air on a daily basis for equivalent lengths of time as controls (no TS exposure).

Bronchoalveolar Lavage (BAL) Analysis

Bronchoalveolar lavage was performed as follows: the trachea was cannulated using a Portex nylon intravenous cannula (pink luer fitting) shortened to approximately 8 mm. Phosphate buffered saline (PBS) was used as the lavage fluid. A volume of 0.4 ml was gently instilled and withdrawn 3 times using a 1 ml syringe and then placed in an Eppendorf tube and kept on ice prior to subsequent determinations.

Cell Counts:

Lavage fluid was separated from cells by centrifugation and the supernatant decanted and frozen for subsequent analysis. The cell pellet was re-suspended in a known volume of PBS and total cell numbers calculated by counting a stained (Turks stain) aliquot under a microscope using a haemocytometer.

Differential cell counts were performed as follows:

The residual cell pellet was diluted to approximately $10^5$ cells per ml. A volume of 500 μl was placed in the funnel of a cytospin slide and centrifuged for 8 min at 800 rpm. The slide was air dried and stained using 'Kwik-Diff' solutions (Shandon) as per the proprietary instructions. When dried and cover-slipped, differential cells were counted using light microscopy. Up to 400 cells were counted by unbiased operator using light microscopy. Cells were differentiated using standard morphometric techniques.

Drug Treatment

Rodents such as mice and rats are obligate nasal breathers thus oral delivery of test materials (such as therapeutic agents) for inhalation will not produce good lung exposure. As a consequence, delivery of therapeutic agents to the lungs in rodents is generally achieved by intra-nasal, intra-tracheal or inhalation by whole body aerosol exposure in a chamber.

The chamber method utilises large amounts of test material and is generally reserved for inhalation toxicology studies rather than pharmacological efficacy studies. Intra-tracheal administration is a very efficient delivery method as almost all of the test material is delivered to the lungs, but this is quite an invasive technique. For studies in the mouse particularly, it is also quite technically demanding as the diameter of the trachea is quite small. The intranasal route is less invasive than the intra-tracheal route and so is particularly suitable for repeat dosing studies such as the 4-11 day mouse model described below. Following intranasal administration ~50% of the dose administered is delivered to the lungs (Eyles J E, Williamson E D and Alpar H O. 1999, Int J Pharm, 189(1): 75-9).

As a surrogate route for oral inhalation, mice were dosed intra-nasally with vehicle (0.2% tween 80 in saline), Example 10 (30 μg/kg), Example 10 (100 μg/kg) or Example 10 (300 μg/kg). The control group of mice received vehicle 1 hr prior to being exposed to air daily for a maximum of 50 minutes per day. TS exposure was conducted for 4 days. BAL was performed 24 h following the final TS exposure.

Data Management and Statistical Analysis

All results are presented as individual data points for each animal and the mean value was calculated for each group. Since tests for normality were positive, the data were subjected to a one way analysis of variance test (ANOVA), followed by a Bonferroni correction for multiple comparisons in order to test for significance between treatment groups. A "p" value of <0.05 was considered to be statistically significant.

Percentage inhibitions were automatically calculated within the Excel spreadsheets for the cell data using the formula below:

$$\% \text{ Inhibition} = 1 - \left( \frac{\text{Treatment group result} - \text{sham group result}}{TS \text{ vehicle group result} - \text{sham group result}} \right) \times 100$$

Inhibition data for other parameters were calculated manually using the above formula.

BRIEF DESCRIPTION OF THE FIGURES

As illustrated in FIG. 1, Example 10 significantly inhibited the BAL cell influx induced by TS at 30, 100 or 300 μg/kg when administered by the intranasal route. Similar findings were observed with BAL neutrophils (FIG. 2).

Figure 1:
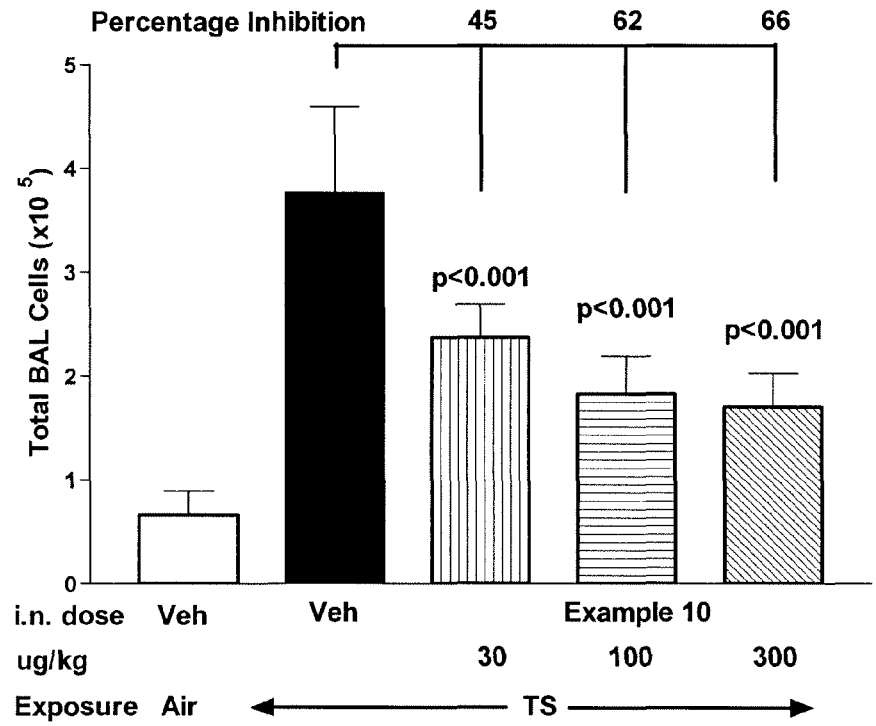
FIG. 1 is a bar graph that illustrates the effect of intranasal administration to laboratory mice with vehicle (0.2% tween 80 in saline), Example 10 (30 μg/kg), Example 10 (100 μg/kg) or Example 10 (300 μg/kg) on the number of BAL cells induced by tobacco smoke 24 hours post the final exposure.
Figure 2:
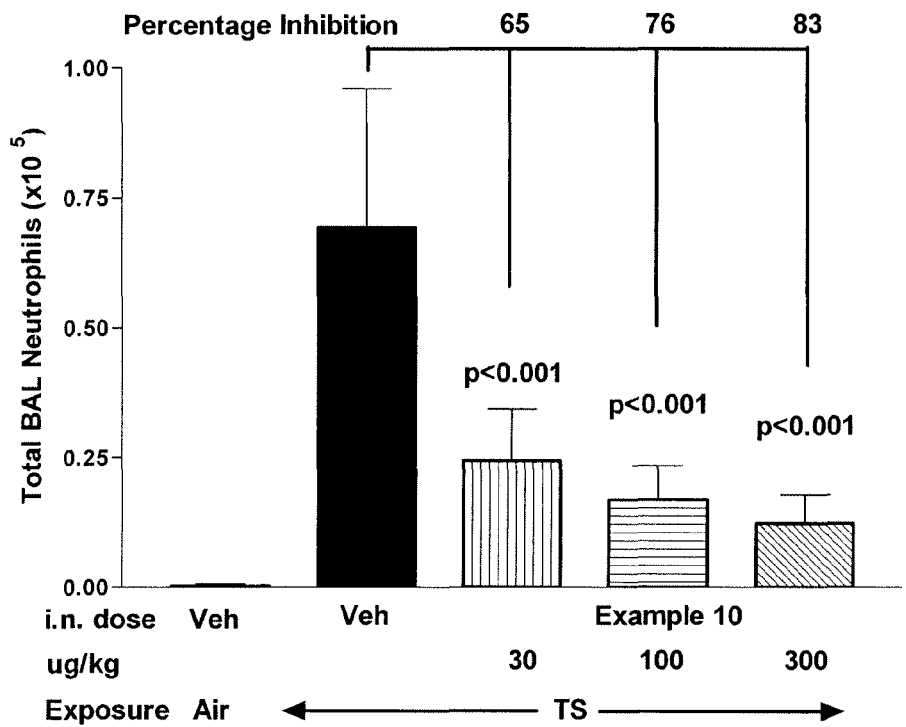
FIG. 2 is a bar graph that illustrates the effect of intranasal administration to laboratory mice with vehicle (0.2% tween 80 in saline), Example 10 (30 μg/kg), Example 10 (100 μg/kg) or Example 10 (300 μg/kg) on the number of BAL neutrophils induced by tobacco smoke 24 hours post the final exposure.

The results demonstrate a clear anti-inflammatory effect in the lungs of mice exposed to TS.

The invention claimed is:

1. A compound of formula (I), or a pharmaceutically acceptable salt thereof:

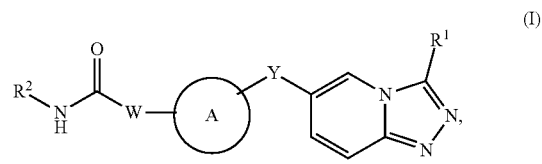

(I)

wherein $R^1$ is $C_1$-$C_6$ alkyl, $C_3$-$C_6$ cycloalkyl, phenyl which is optionally substituted, 5- or 6-membered monocyclic heteroaryl which is optionally substituted, or a radical of formula (II)

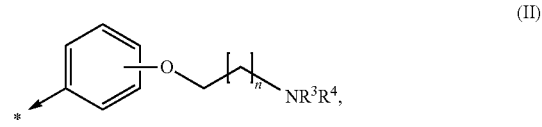

(II)

wherein n is 1 or 2, and $R^3$ and $R^4$ are independently H or $C_1$-$C_6$ alkyl, or $R^3$ and $R^4$ taken together with the nitrogen to which they are attached form a 6-membered heterocyclic ring optionally comprising a further heteroatom selected from N and O;

Y is —O— or —S(O)$_p$— wherein p is 0, 1, or 2;

A is an optionally substituted divalent arylene radical, a monocyclic heteroaryl radical, a bicyclic heteroarylene radical, a $C_3$-$C_6$ divalent cycloalkylene radical having 5 or 6 ring atoms, or a piperidinylene radical wherein the ring nitrogen is linked to $R^2$NHC(=O)W—;

W is a bond, —NH— or —C(R$^A$)(R$^B$), wherein R$^A$ and R$^B$ are independently H, methyl, ethyl, amino, hydroxyl, or halo; and R$^2$ is a radical of formula (IIIA), (IIIB), or (IIIC):

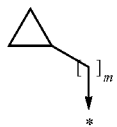
(IIIA)

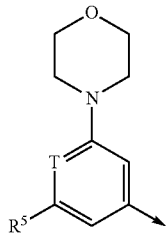
(IIIB)

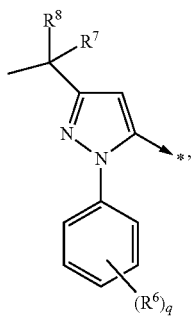
(IIIC)

wherein
m is 0 or 1,
q is 0, 1, 2, or 3,
T is —N= or —CH=,
R$^5$ is H or F,
R$^7$ is —CH$_3$, —C$_2$H$_5$, —CH$_2$OH, —CH$_2$SCH$_3$, —SCH$_3$, or -SC$_2$H$_5$,
R$^8$ is —CH$_3$ or —C$_2$H$_5$, and
each occurrence of R$^6$ is independently H, C$_1$-C$_6$, hydroxyl, or halo;
or a single occurrence or R$^6$ is a radical of formula (IVA), (IVB), or (IVC)

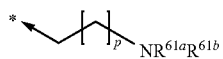
(IVA)

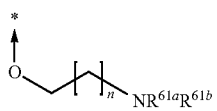
(IVB)

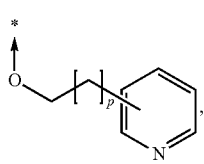
(IVC)

while any other occurrence of R$^6$ is independently H, C$_1$-C$_6$ alkyl, hydroxyl or halo;

and wherein, in R$^6$,

R$^{61a}$ and R$^{61b}$ are H, alkyl, or R$^{61a}$ and R$^{61b}$ are optionally joined together with the nitrogen to which they are attached to form a heterocyclic ring optionally comprising a further heteroatom selected from N and O.

2. A compound, or a pharmaceutically acceptable salt thereof, of claim 1 wherein the divalent radical —W-[A]-Y— has one of formulae (B)-(J):

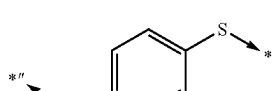
(B)

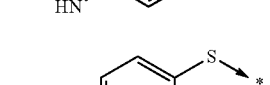
(C)

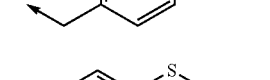
(D)

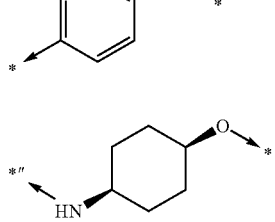
(E)

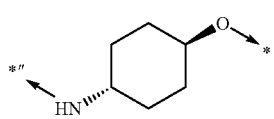
(F)

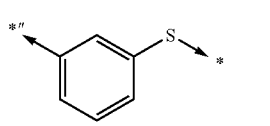
(G)

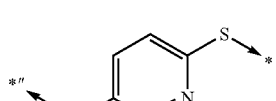
(H)

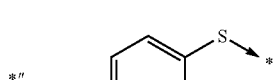
(I)

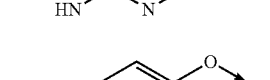
(J)

3. A compound, or a pharmaceutically acceptable salt thereof, of claim 1, having formula (IA):

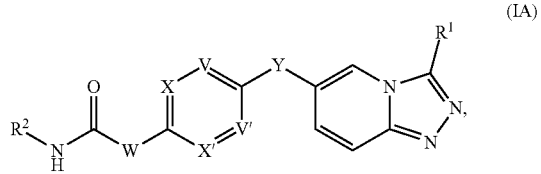

wherein V, V', X and X' are independently —CH= or —N=.

4. The compound, or a pharmaceutically acceptable salt thereof, of claim 1, having formula (IA¹):

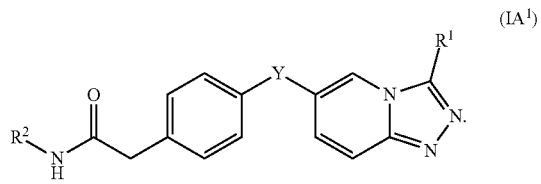

5. A compound, or a pharmaceutically acceptable salt thereof, of claim 1, having formula (IB):

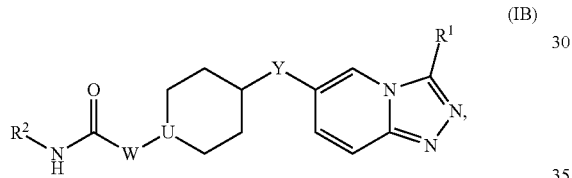

wherein
U is CH or N,
with the proviso that when U is N, then W is not NH.

6. A compound, or a pharmaceutically acceptable salt thereof, of claim 1, having formula (IB¹):

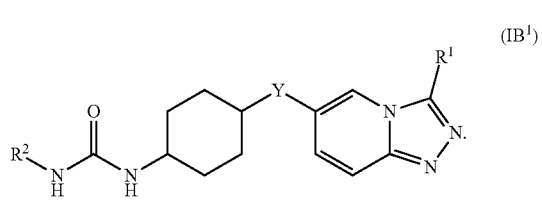

7. A compound, or a pharmaceutically acceptable salt thereof, of claim 1, having formula (IC):

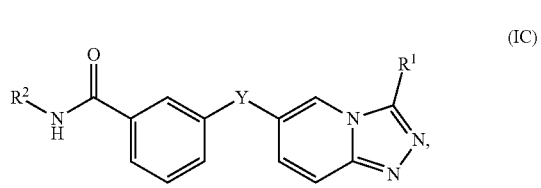

wherein $R^1$ is phenyl, 5- or 6-membered monocyclic heteroaryl or a radical of formula (II).

8. A compound, or a pharmaceutically acceptable salt thereof, of claim 1, wherein $R^1$ is a group of formula (II) wherein the group —$NR^3R^4$ is morpholinyl.

9. A compound, or a pharmaceutically acceptable salt thereof, of claim 1, wherein $R^1$ is isopropyl.

10. A compound, or a pharmaceutically acceptable salt thereof, of claim 1, wherein $R^2$ is a radical of formula (IIIC), and wherein $R^7$ and $R^8$ are each methyl.

11. A compound, or a pharmaceutically acceptable salt thereof, of claim 1, wherein $R^2$ has formula (IIID), (IIIE), (IIIF), or (IIIG):

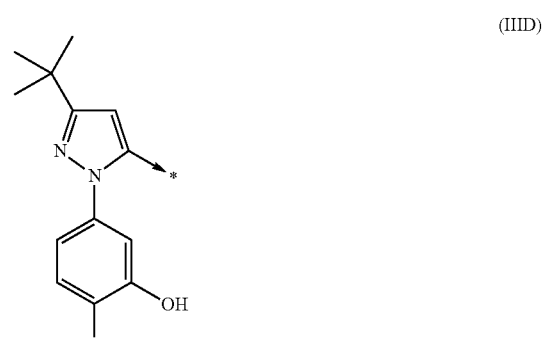

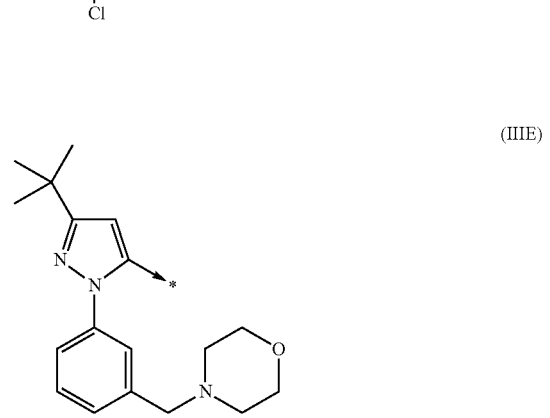

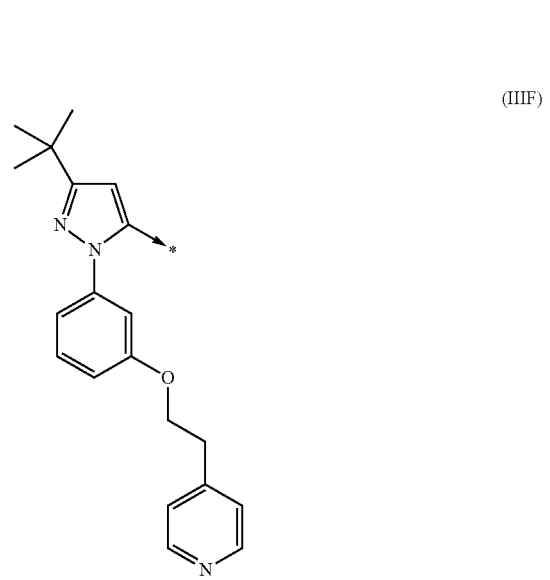

-continued

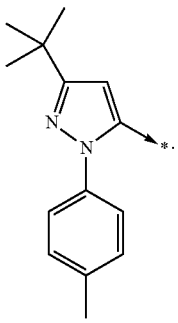

(IIIG)

12. A compound, or a pharmaceutically acceptable salt thereof, of claim 1, wherein $R^2$ is a radical of formula (IIIA), and
wherein m is 0.

13. A compound, or a pharmaceutically acceptable salt thereof, of claim 1, wherein $R^2$ is a radical of formula (IIIB), and
wherein (a) T is —CH= and $R^5$ =H.

14. A pharmaceutical composition, comprising:
a compound, or a pharmaceutically acceptable salt thereof, of claim 1, together with at least one selected from the group consisting of a pharmaceutically acceptable carrier and a pharmaceutically acceptable excipient.

15. A composition of claim 14, which is adapted for inhalation for pulmonary administration.

16. A method of treating a disease or a condition which benefits from the inhibition of p38 MAP kinase activity, the method comprising administering to a subject in need thereof, an effective amount of a compound, or a pharmaceutically acceptable salt thereof, of claim 1.

17. The method of claim 16, wherein the disease or condition is chronic eosinophilic pneumonia, asthma, COPD, adult respiratory distress syndrome (ARDS), exacerbation of airways hyper-reactivity consequent to other drug therapy, or an airways disease that is associated with pulmonary hypertension.

18. A compound, or a pharmaceutically acceptable salt thereof, of claim 1, wherein $R^1$ is 2,6-dichlorophenyl.

19. A compound, or a pharmaceutically acceptable salt thereof of claim 1, wherein $R^2$ is a radical of formula (IIIB), and
wherein (b) T is —N= and $R^5$ =H.

20. A compound, or a pharmaceutically acceptable salt thereof, of claim 1, wherein $R^2$ is a radical of formula (IIIB), and
wherein (c) T—CH= and $R^5$ =F.

* * * * *